(12) United States Patent
Förster

(10) Patent No.: US 9,409,859 B2
(45) Date of Patent: Aug. 9, 2016

(54) SUBSTITUTED DIPHENYL DERIVATIVES

(75) Inventor: Heinz Förster, Kadenbach (DE)

(73) Assignee: CREATIVE THERAPEUTICS GMBH, Wuppertal (DE)

( * ) Notice: Subject to any disclaimer, the term of this patent is extended or adjusted under 35 U.S.C. 154(b) by 217 days.

(21) Appl. No.: 14/005,395

(22) PCT Filed: Mar. 12, 2012

(86) PCT No.: PCT/DE2012/000258
§ 371 (c)(1),
(2), (4) Date: Sep. 16, 2013

(87) PCT Pub. No.: WO2012/122969
PCT Pub. Date: Sep. 20, 2012

(65) Prior Publication Data
US 2014/0005149 A1    Jan. 2, 2014

(30) Foreign Application Priority Data

Mar. 16, 2011   (DE) .......................... 10 2011 014 087

(51) Int. Cl.
| | |
|---|---|
| C07C 305/24 | (2006.01) |
| C07C 309/63 | (2006.01) |
| C07C 307/02 | (2006.01) |
| C07C 317/34 | (2006.01) |
| C07C 323/48 | (2006.01) |
| C07D 311/36 | (2006.01) |
| C07C 303/30 | (2006.01) |
| C07C 303/40 | (2006.01) |
| C07C 311/00 | (2006.01) |
| C07D 311/38 | (2006.01) |

(52) U.S. Cl.
CPC ............. *C07C 309/63* (2013.01); *C07C 303/30* (2013.01); *C07C 303/40* (2013.01); *C07C 305/24* (2013.01); *C07C 307/02* (2013.01); *C07C 311/00* (2013.01); *C07C 317/34* (2013.01); *C07C 323/48* (2013.01); *C07D 311/36* (2013.01); *C07D 311/38* (2013.01)

(58) Field of Classification Search
CPC .................................................... C07C 305/24
See application file for complete search history.

(56) References Cited

U.S. PATENT DOCUMENTS

| | | | |
|---|---|---|---|
| 2,648,660 A | 8/1953 | Lance | |
| 2010/0234327 A1* | 9/2010 | Reiter et al. | ................... 514/150 |

FOREIGN PATENT DOCUMENTS

| | | | | |
|---|---|---|---|---|
| GB | 1371969 | * | 10/1974 | ............ C07C 115/00 |
| WO | 2009004060 | | 1/2009 | |
| WO | WO2009004060 | * | 1/2009 | ............ C07C 245/24 |

OTHER PUBLICATIONS

Golob et al. (Bioorg. Med. Chem. 10 (2002) 3941-3953).*
Nussbaumer et al. (Bioorg. Med. Chem. Lett. 12 (2002) 2093-2095).*
Winum et al. (Medicinal Research Reviews, vol. 25, No. 2, 186-228, 2005).*

* cited by examiner

*Primary Examiner* — Robert Havlin
(74) *Attorney, Agent, or Firm* — Edward E. Sowers; Brannon Sowers & Cracraft PC

(57) ABSTRACT

Triazene-substituted diphenyl derivatives are suitable as chemotherapeutic agents for treating carcinomas in humans and animals.

2 Claims, No Drawings

SUBSTITUTED DIPHENYL DERIVATIVES

CROSS-REFERENCES TO RELATED APPLICATIONS

This application is a National Stage filing of International Application PCT/DE2012/000258, filed Mar. 12, 2012, claiming priority to German Applications No. DE 10 2011 014 087.5 filed Mar. 16, 2011, entitled "Substituted Diphenyl Derivatives." The subject application claims priority to PCT/DE2012/000258, and to German Applications No. DE 10 2011 014 087.5 and incorporates all by reference herein, in their entirety.

BACKGROUND OF THE INVENTION

The present invention relates to substituted diphenyl derivatives containing at least (i) a dialkyltriazenyl group, (ii) at least one sulfooxy group and/or at least one sulfamoyloxy group per molecule, their salts, solvates and the solvates of these salts. The invention further relates to a process for preparing these compounds and to their use as medicaments.

For the purposes of the present invention, diphenyl derivatives are phenyl rings joined by a single bond or by a bridge.

Triazene-substituted diphenyl derivatives are known. Thus, DE 17 93 115 A1, DE 21 47 781 A1 and WO 2004/106358 A1 disclose, inter alia, diphenyl derivatives which are substituted by triazene groups and, for example, sulfonic acid or oxycarboxylic acid groups.

Triazene derivatives have in past decades been comprehensively examined for their cytostatic effectiveness. These conventional triazene cytostatics belong to the group of alkylating compounds and, owing to their severe side effects and toxicity, have never found wide clinical use. An exception is dacarbazine (DTIC) which is a prodrug of monomethyl-triazenoimidazolecarboxamide (MTIC) and is used mainly for combating Hodgkin's lymphoma and soft tissue sarcomas (Cancer Treatment Reports 60, 205-211 (1976)). Owing to the light sensitivity of dacarbazine and in particular its side effects, among which leucopenia and thrombopenia are particularly important, a large number of arylalkyltriazenes have been studied with the aim of synthesizing more potent and better tolerable triazenes (Cancer Treatment Reports 60: 125-134 (1976); J. Med. Chem. 23, 1052-1024 (1980)). Despite these efforts, dacarbazine and temozolomide are to date the only triazenes remaining in clinical use of the treatment of glioblastomas, even though they are associated with considerable side effects such as bone marrow depression, neurotoxicity and liver toxicity, emesis, hair loss and exanthems.

A first attempt to overcome the tolerability problems of selected triazenes with a view to selective use in the case of breast cancer is described in DE 17 93 115 A1 and DE 21 47 781 A1.

A second attempt to overcome severe side effects of selected triazenes is described in WO 2004/106358 A1. Some severe side effects of the known triazenes are said to be reduced by introduction of oxycarboxylic acid groups. However, owing to undesirable side effects on the kidney they are not suitable for long-term use.

BRIEF SUMMARY OF THE INVENTION

It is an object of the present invention to provide oncocidal active compounds which are suitable for long-term therapy virtually without toxic side effects and with at the same time improved effectiveness.

We have found new diphenyl derivatives containing (i) at least one dialkyltriazenyl group and (ii) at least one sulfooxy group and/or at least one sulfamoyloxy group per molecule, and their salts, solvates and solvates of these salts.

The novel diphenyl derivatives of the invention surprisingly have a greatly improved antitumor effect in the case of tumors of important target organs (e.g. colon, lung, liver, pancreas, kidney), in particular as selective oncocides against tumors of the skin, breast, prostate and testicle and also of the target organs dependent on sex hormones compared to similar known active compounds (WO 2004/106358 A1, DE 17 93 115 A1 and DE 21 47 781 A1). Compared to similar known active compounds, they are virtually without toxic side effects and are thus suitable for long-term therapy.

Owing to their better tolerability combined with a high effectiveness, they are medically useful both as monotherapy and also in combination with other carcinostatics, tumor-specific antibodies or antibodies which are coupled via linkers to the compounds according to the invention.

Intracellularly, they liberate a proliferation-inhibiting/oncocidal effective principle which can stop the uncontrolled replicative metabolism of the tumor cells and even lead to regression of the tumor.

The novel diphenyl derivatives can be used as active compounds in medicaments for human beings and animals.

Diphenyltriazenes having sulfuric acid and sulfuric acid amide groups in the molecule have not been described and there is no indication of particular effectiveness.

DETAILED DESCRIPTION OF THE INVENTION

For the purposes of the present invention, preference is given to substituted diphenyl derivatives of the formula

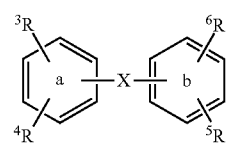

(1)

where
X is a direct C—C bond between the rings a and b, CH$_2$, CHOH, CO, S, SO, SO$_2$, —N=N—, —CR$^7$=CR$^8$— or a divalent —C(O)—C*=CH—O— radical which together with the two adjacent carbon atoms of the ring a on which it is located forms a pyranone ring, with the ring b being located on the C* atom of this radical, R$^3$, R$^6$ are each, independently of one another, hydrogen, hydroxyl, C$_1$-C$_4$-alkyl, C$_1$-C$_4$-alkoxy, C$_1$-C$_4$-alkyl-S—, C$_1$-C$_4$-alkyl-SO—, C$_1$-C$_4$-alkyl-SO$_2$—, where alkyl is preferably methyl or ethyl, halogen (F, Cl, Br, I), nitro, cyano or an —OSO$_2$Y group, R$^4$, R$^5$ are each, independently of one another, an —N=N—N(R$^2$)$_2$ group or an —OSO$_2$Y group, R$^7$ is hydrogen, methyl, ethyl or a phenyl radical which is substituted by the radicals R$^9$-R$^{10}$ and is bound directly to the R$^7$-bearing carbon atom, R$^8$ is hydrogen, ethyl, CN, NO$_2$, —CH$_2$CH$_2$-halogen (F, Cl, Br, I) or CH$_2$CH$_2$OH, R$^9$, R$^{10}$ are each, independently of one another, hydrogen, hydroxyl, C$_1$-C$_4$-alkyl, C$_1$-C$_4$-alkoxy, where alkyl is preferably methyl or ethyl, halogen (F, Cl, Br, I), nitro, cyano, an —N=N—N(R$^2$)$_2$ group or an —OSO$_2$Y group, Y is OH or N(R$^1$)$_2$, $R^1$ is hydrogen, methyl or ethyl and $R^2$ is methyl or ethyl, with the proviso that, per total molecule (1), one or two —N=N—N($R^2$)$_2$ groups and one or two —OSO$_2$Y groups are located on any ring carbons of aromatic rings, and also their salts, free acids, solvates and the solvates of these salts and the solvates of these free acids.

We have also found a process for preparing the novel diphenyl derivatives containing (i) at least one dialkyltriazenyl group and (ii) at least one sulfooxy group and/or at least one sulfamoyloxy group per molecule and their salts, solvates and solvates of these salts, which is characterized in that aminophenyl derivatives of the formula

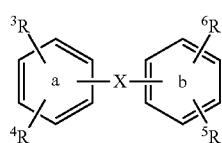

(2)

where

X is a direct C—C bond, CH$_2$, CHOH, CO, S, SO, SO$_2$, —N=N—, —CR$^7$=CR$^8$— or a divalent —C(O)—C*=CH—O— radical which together with the two adjacent carbon atoms of the ring a on which it is located forms a pyranone ring, with the ring b being located on the C* atom of this radical, $R^3$, $R^6$ are each, independently of one another, hydrogen, hydroxyl, $C_1$-$C_4$-alkyl, $C_1$-$C_4$-alkoxy, $C_1$-$C_4$-alkyl-SO—, $C_1$-$C_4$-alkyl-SO$_2$—, where alkyl is preferably methyl or ethyl, halogen (F, Cl, Br, I), nitro, cyano or an —OSO$_2$Y group, $R^4$, $R^5$ are each, independently of one another, an —NH$_2$ group or an —OSO$_2$Y group, $R^7$ is hydrogen, methyl, ethyl or a phenyl radical which is substituted by the radicals $R^9$, $R^{10}$ and is bound directly to the $R^7$-bearing carbon atom, $R^8$ is hydrogen, ethyl, CN, NO$_2$, —CH$_2$CH$_2$-halogen (F, Cl, Br, I) or CH$_2$CH$_2$OH, $R^9$, $R^{10}$ are each, independently of one another, hydrogen, hydroxyl, $C_1$-$C_4$-alkyl, preferably methyl or ethyl, $C_1$-$C_4$-alkoxy, preferably methoxy or ethoxy, halogen (F, Cl, Br, I), nitro, cyano, an —NH$_2$ group or an —OSO$_2$Y group, Y is OH or N($R^1$)$_2$, and $R^1$ is hydrogen, methyl or ethyl, with the proviso that, per total molecule (2), one or two NH$_2$ groups and one or two —OSO$_2$Y groups are located on any ring carbons of aromatic rings, are diazotized by means of a diazotizing agent in the presence of strong acid at low temperature, preferably from 0 to 8° C., particularly preferably from 0 to 5° C. and in particular from 0 to 2° C., in aqueous-acidic solution to form diazonium salts of the formula

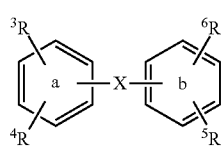

(3)

where

X is a direct C—C bond, CH$_2$, CHOH, CO, S, SO, SO$_2$, —N=N—, —CR$^7$=CR$^8$— or a divalent —C(O)—C*=CH—O— radical which together with the two adjacent carbon atoms of the ring a on which it is located forms a pyranone ring, with the ring b being located on the C* atom of this radical, $R^3$, $R^6$ are each, independently of one another, hydrogen, hydroxyl, $C_1$-$C_4$-alkyl, $C_1$-$C_4$-alkoxy, $C_1$-$C_4$-alkyl-S—, $C_1$-$C_4$-alkyl-SO—, $C_1$-$C_4$-alkyl-SO$_2$—, where alkyl is preferably methyl or ethyl, halogen (F, Cl, Br, I), nitro, cyano or an —OSO$_2$Y group, $R^4$, $R^5$ are each, independently of one another, an —N$_2^+$AN$^-$ group or an —OSO$_2$Y group, $R^7$ is hydrogen, methyl, ethyl or a phenyl radical which is substituted by the radicals $R^9$, $R^{10}$ and is bound directly to the $R^7$-bearing carbon atom, $R^8$ is hydrogen, ethyl, CN, NO$_2$, —CH$_2$CH$_2$-halogen (F, Cl, Br, I) or CH$_2$CH$_2$OH, $R^9$, $R^{10}$ are each, independently of one another, hydrogen, hydroxyl, $C_1$-$C_4$-alkyl, $C_1$-$C_4$-alkoxy, where alkyl is preferably methyl or ethyl, halogen (F, Cl, Br, I), nitro, cyano, an —N$_2^+$AN$^-$ group or an —OSO$_2$Y group, AN$^-$ is a halogen anion (Cl$^-$, Br$^-$) or ½ sulfate (SO$_4^{2-}$) anion, Y is OH or N($^1$R)$_2$, $R^1$ is hydrogen, methyl or ethyl, with the proviso that, per total molecule (3), one or two diazonium groups and one or two —OSO$_2$Y groups are located on any ring carbons of aromatic rings, and the diazonium salts (3) obtained are then reacted with dialkylamines of the formula $$HN(R^2)_2 \qquad (4)$$

where R$_2$ is methyl or ethyl, in the presence of acid binding agents, optionally followed by preparation of the salts from the compounds obtained and optionally followed by setting-free of the hydroxyl and/or acid groups from these salts.

Suitable diluents for the diazotization reaction are all polar solvents which are inert under the reaction conditions, e.g. alcohols such as methanol, ethanol, also dimethylformamide and dimethyl sulfoxide and in particular water or mixtures of these solvents.

As strong acid in the diazotization reaction, it is possible to use hydrohalic acids, preferably hydrochloric acid, or sulfuric acid.

As diazotizing agents, preference is given to potassium nitrite and sodium nitrite.

As acid acceptors in the coupling reaction, it is possible to use all customary acid binding agents. These preferably include sodium carbonate and potassium carbonate.

For the purposes of the invention, salts are preferably physiologically acceptable salts. They include salts of customary bases, for example alkali metal salts (e.g. sodium salts and potassium salts), alkaline earth metal salts (e.g. calcium salts and magnesium salts) and ammonium salts derived from ammonia or organic $C_1$-$C_{16}$-amines such as ethylamine, diethylamine, triethylamine, ethyldiisopropylamine, monoethanolamine, diethanol-amine, trishydroxyethylamine, dicyclohexylamine, dimethylaminoethanol, dibenzylamine, N-methyl-morpholine, dihydroabietylamine, arginine, lysine, ethylenediamine and methylpiperidine.

For the purposes of the invention, solvates are forms of the compounds which in the solid or liquid state form a complex by coordination of solvent molecules. Hydrates are a specific form of solvates in which water is coordinated.

As an alternative, the diphenyl derivatives of the invention can also be prepared by firstly introducing the triazenyl groups and only then introducing sulfooxy and/or sulfamoyloxy groups. For this purpose, triazenylphenols of the formula

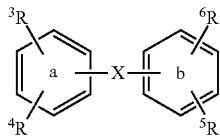
(2a)

where

X is a direct C—C bond, $CH_2$, CHOH, CO, S, SO, $SO_2$, —N=N—, —$CR_7$=$CR_8$— or a divalent —C(O)—C*=CH—O— radical which together with the two adjacent carbon atoms of the ring a on which it is located forms a pyranone ring, with the ring b being located on the C* atom of this radical, $R^3$, $R^6$ are each, independently of one another, hydrogen, hydroxyl, $C_1$-$C_4$-alkyl, $C_1$-$C_4$-alkoxy, $C_1$-$C_4$-alkyl-S—, $C_1$-$C_4$-alkyl-SO—, $C_1$-$C_4$-alkyl-$SO_2$—, where alkyl is preferably methyl or ethyl, halogen (F, Cl, Br, I), nitro, cyano or an OH group, $R^4$, $R^5$ are each, independently of one another, an —N=N—N($R^2$)$_2$ group or an OH group, $R^7$ is hydrogen, methyl, ethyl or a phenyl radical which is substituted by the radicals $R^9$, $R^{10}$ and is bound directly to the $R^7$-bearing carbon atom, $R^8$ is hydrogen, ethyl, CN, $NO_2$, —$CH_2CH_2$-halogen (F, Cl, Br, I) or $CH_2CH_2OH$, $R^9$, $R^{10}$ are each, independently of one another, hydrogen, hydroxyl, $C_1$-$C_4$-alkyl, $C_1$-$C_4$-alkoxy, where alkyl is preferably methyl or ethyl, halogen (F, Cl, Br, I), nitro, cyano, an —N=N—N($R^2$)$_2$ group or an OH group, Y is OH or N($R^1$)$_2$ and $R^1$ is hydrogen, methyl or ethyl, with the proviso that, per total molecule (2), one or two —N=N—N($R^2$)$_2$ groups and one or two OH groups are located on any ring carbons of aromatic rings, can then be sulfated or sulfoamidated.

The diphenyl derivatives of the invention are described in detail below depending on the definition of X:

1. cis- and Trans-Stilbenes of the Formula (5)

When X in formula (1) is —$CR^7$=$CR^8$—, the compounds of the invention have the formula

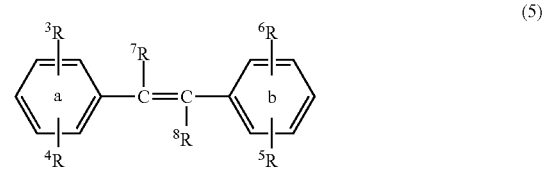
(5)

where $R^3$, $R^6$ are each, independently of one another, hydrogen, hydroxyl, $C_1$-$C_4$-alkyl, $C_1$-$C_4$-alkoxy, $C_1$-$C_4$-alkyl-S—, $C_1$-$C_4$-alkyl-SO—, $C_1$-$C_4$-alkyl-$SO_2$—, where alkyl is preferably methyl or ethyl, halogen (F, Cl, Br, I), nitro, cyano or an —$OSO_2Y$ group, $R^4$, $R^5$ are each, independently of one another, an —N=N—N($R^2$)$_2$ group or an —$OSO_2Y$ group, $R^7$ is hydrogen, methyl, ethyl or a phenyl radical which is substituted by the radicals $R^9$, $R^{10}$ and is bound directly to the $R^7$-bearing carbon atom, $R^8$ is hydrogen, ethyl, CN, $NO_2$, —$CH_2CH_2$-halogen (F, Cl, Br, I) or $CH_2CH_2OH$, $R^9$, $R^{10}$ are each, independently of one another, hydrogen, hydroxyl, $C_1$-$C_4$-alkyl, $C_1$-$C_4$-alkoxy, where alkyl is preferably methyl or ethyl, halogen (F, Cl, Br, I), nitro, cyano, an —N=N—N($R^2$)$_2$ group or an —$OSO_2Y$ group, Y is OH or N($R^1$)$_2$, $R^1$ is hydrogen, methyl or ethyl and $R^2$ is methyl or ethyl, with the proviso that, per total molecule (5), one or two —N=N—N($R^2$)$_2$ groups and one or two —$OSO_2Y$ groups are located on any ring carbons of aromatic rings, and also their salts, free acids, solvates and the solvates of these salts and the solvates of these free acids.

Preference is given to compounds of the formula (5) in which $R^4$, $R^5$ are each a $(CH_3)_2$N—N=N— group in the 3 position and in the 3' position, $R^3$, $R^6$ are each an —$OSO_2Y$ group in the 4 position and in the 4' position, $R^7$, $R^8$ are each ethyl and Y is OH or $NH_2$, with the proviso that, per total molecule (5), one or two —N=N—N($CH_2$)$_2$ and one or two —$OSO_2Y$ groups are located on any ring carbons of aromatic rings, and also their salts, free acids, solvates and the solvates of these salts and the solvates of these free acids.

Furthermore, preference is given to compounds of the formula (5) in which $R^4$, $R^5$ are each, independently of one another, hydrogen, a $(CH_3)_2$N—N=N— group or an —$OSO_2Y$ group, $R^3$, $R^6$ are each, independently of one another, hydrogen, fluorine, chlorine, hydroxyl, methyl, methoxy or an —$OSO_2Y$ group, $R^7$, $R^8$ are each hydrogen and Y is OH or $NH_2$, with the proviso that, per total molecule (5), one or two —N=N—N($CH_2$)$_2$ and one or two —$OSO_2Y$ groups are located on any ring carbons of aromatic rings, and also their salts, free acids, solvates and the solvates of these salts and the solvates of these free acids.

Particular preference is given to compounds of the formula (5) in which $R^3$ is hydrogen, hydroxy or an —$OSO_2Y$ group in the 4 position, $R^4$ is an —$OSO_2Y$ group in the 2 position, $R^5$ is a $(CH_3)_2$N—N=N— group in the 4' position, $R^6$ is hydrogen or methyl in the 2' position, $R^7$, $R^8$ are each hydrogen and Y is OH or $NH_2$, with the proviso that, per total molecule (5), one or two —N=N—N($CH_2$)$_2$ and one or two —$OSO_2Y$ groups are located on any ring carbons of aromatic rings, and also their salts, free acids, solvates and the solvates of these salts and the solvates of these free acids.

As particularly preferred stilbenes (5) for the purposes of the invention, mention may be made of the following compounds:

(Z+E) 4-(3,3-dimethyltriazenyl-1)-4'-sodiosulfooxy-2'-sulfamoyloxystilbene

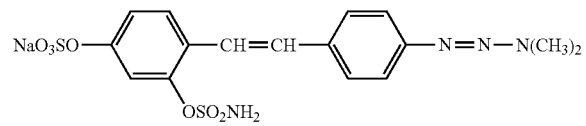

(Z+E) 4-(3,3-dimethyltriazenyl-1)-4'-hydroxy-2'-sodiosulfooxystilbene

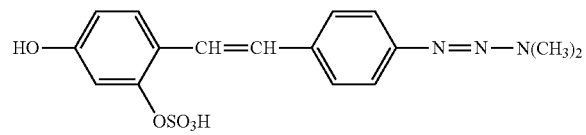

(Z and E) 4-(dimethyltriazenyl-1)-2-methyl-4'-hydroxy-2'-sodiosulfooxystilbene

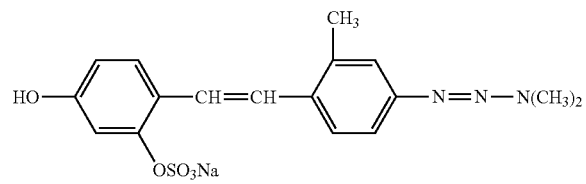

3,3'-[di-(3,3-dimethyltriazenyl-1)]-4,4'-(disodiosulfooxy)-1,2-diethylstilbene

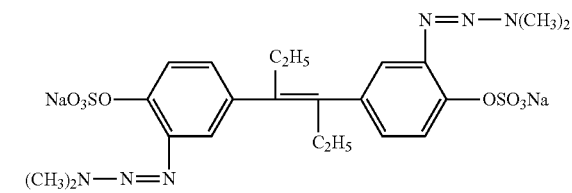

and also their salts, free acids, solvates and the solvates of these salts and the solvates of these free acids.

The compounds (5) can be prepared in a manner analogous to the compounds (1) from the aromatic amines

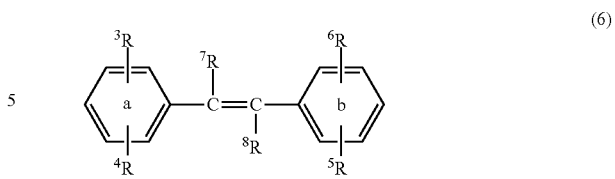

(6)

where
$R^3$, $R^6$ are each, independently of one another, hydrogen, hydroxyl, $C_1$-$C_4$-alkyl, $C_1$-$C_4$-alkoxy, $C_1$-$C_4$-alkyl-S—, $C_1$-$C_4$-alkyl-SO—, $C_1$-$C_4$-alkyl-$SO_2$—, where alkyl is preferably methyl or ethyl, halogen (F, Cl, Br, I), nitro, cyano or an —$OSO_2Y$ group,
$R^4$, $R^5$ are each, independently of one another, an —$NH_2$ group or an —$OSO_2Y$ group,
$R^7$ is hydrogen, methyl, ethyl or a phenyl radical which is substituted by the radicals $R^9$, $R^{10}$ and is bound directly to the $R^7$-bearing carbon atom,
$R^8$ is hydrogen, ethyl, CN, $NO^2$, —$CH_2CH_2$-halogen (F, Cl, Br, I) or $CH_2CH_2OH$,
$R^9$, $R^{10}$ are each, independently of one another, hydrogen, hydroxyl, $C_1$-$C_4$-alkyl, $C_1$-$C_4$-alkoxy, where alkyl is preferably methyl or ethyl, halogen (F, Cl, Br, I), nitro, cyano, an —$NH_2$ group or an —$OSO_2Y$ group,
Y is OH or $N(R^1)_2$ and
$R^1$ is hydrogen, methyl or ethyl,
with the proviso that, per total molecule (6), one or two —$NH_2$ groups and one or two —$OSO_2Y$ groups are located on any ring carbons of aromatic rings.

If, for example, 3,3'-diamino-4,4'-dipotassiosulfooxy-1,2-diethylstilbene, potassium nitrite and dimethylamine are used as starting materials, the course of the reaction can be represented by the reaction scheme

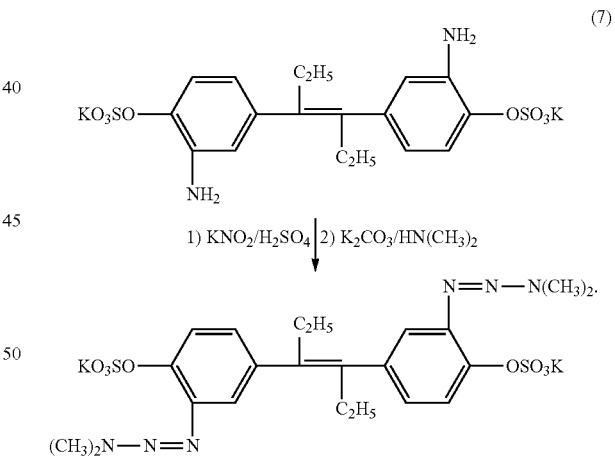

The 3,3'-diamino-4,4'-dipotassiosulfooxy-1,2-diethylstilbene shown in the reaction scheme (7) can be prepared from the known 3,3'-dinitriodiethylstilbestrol (Arch. Pharm. (Weinheim) 311, 184-195 (1978)) with subsequent sulfation and reduction to the diamine.

The aromatic amines (6) can be prepared in a manner known per se from the corresponding nitrosulfooxyaromatics or nitrosulfamoyloxyaromatics by, for example, catalytic reduction by means of hydrogen over palladium/carbon in ethanol or over platinum oxide in methanol (Chem. Berichte. 72, 839, [(1939)]) or using Raney Nickel in THF (Chem. Berichte. 91, 1905 (1958)).

The synthetic methods mentioned here can also be utilized for synthesizing the aromatic amines used in sections 2-4.

Examples of the conversion of aromatic amines into diazonium salts and coupling of these with dialkylamines to form (3,3-dialkyltriazenyl-1)-aryls are comprehensibly described in DE 17 93 115 A1, DE 21 47 781 A1, GB 1 371 969 and WO 2004/106358.

The preparation of the new starting materials having sulfooxy or sulfamoyloxy groups can be carried out by reaction of the corresponding aromatic phenols with alkali metal bisulfate (Na, K) as described in EP 0 722 455 A1/U.S. Pat. No. 5,703,261, optionally alternatively with chlorosulfonic acid/pyridine as described in WO 02/134715 A1 or with sulfamoyl chlorides in dimethylacetamide as described in WO 2008/003378 and US 2003/0225051, page 44.

The syntheses mentioned here can also be used in the reactions according to sections 2-4 in the conversion of phenolic hydroxyl groups into the starting materials or end products according to the invention having sulfooxy or sulfamoyloxy groups.

The synthesis of the compounds according to the invention can be illustrated by the reaction schemes 8 and 9:

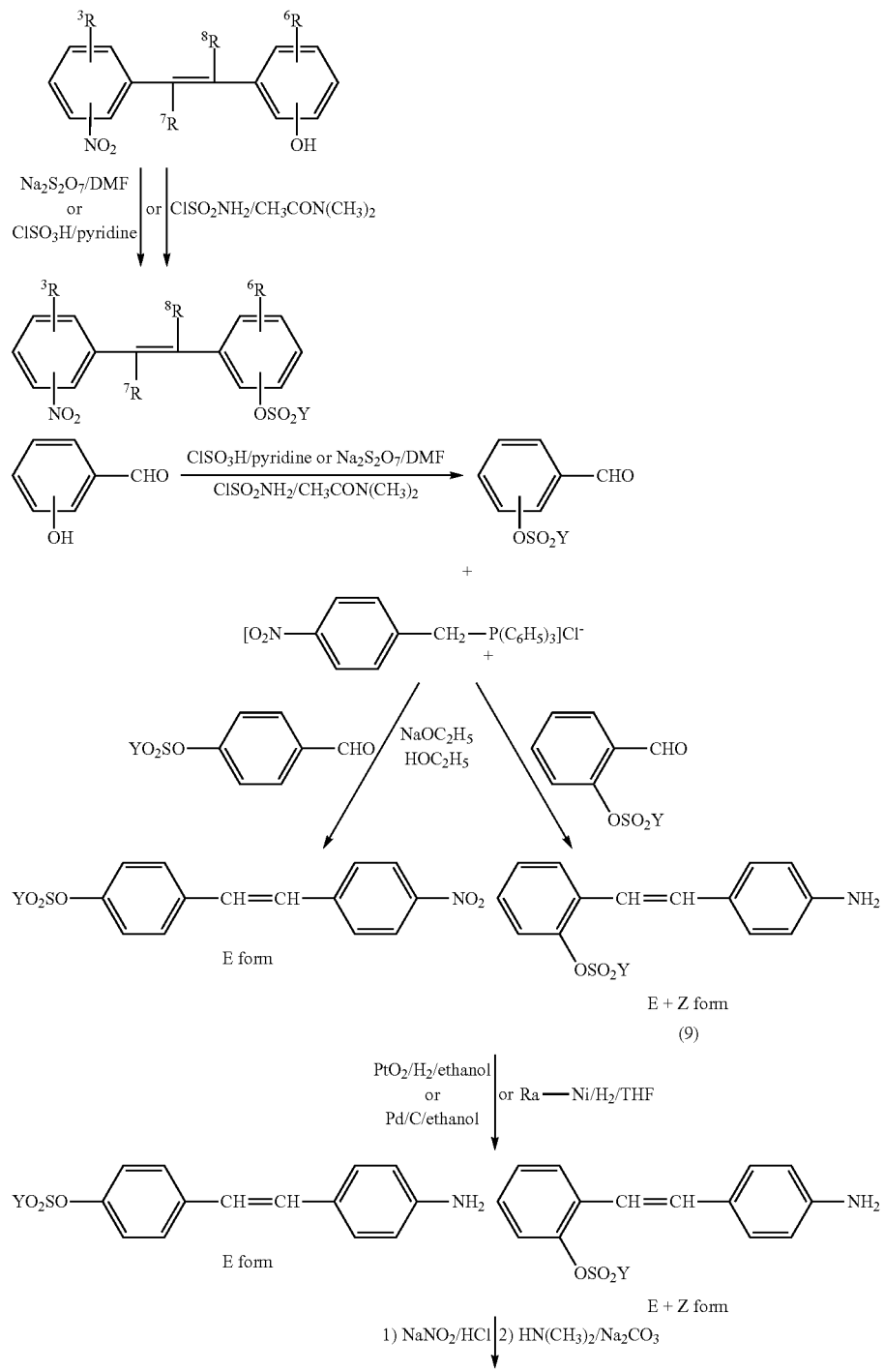

-continued

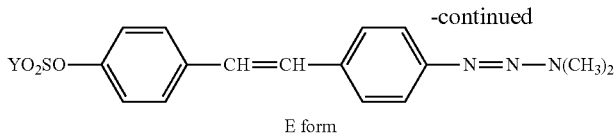

E form

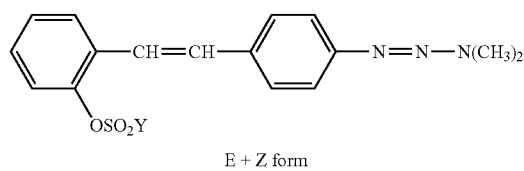

E + Z form

2. Triphenylethylene Derivatives of the Formula (10)

When, in formula (1),

X is —$CR^7$=$CR^8$— and $R^7$ is a phenyl radical which is substituted by $R^9$, $R^{10}$ and is bound directly to the $R^7$-bearing carbon atom, these compounds have the formula

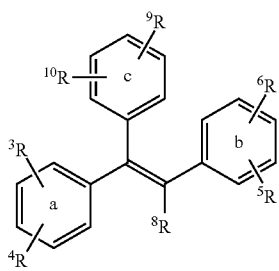

(10)

where $R^3$, $R^6$ are each, independently of one another, hydrogen, hydroxyl, $C_1$-$C_4$-alkyl, $C_1$-$C_4$-alkoxy, $C_1$-$C_4$-alkyl-S—, $C_1$-$C_4$-alkyl-SO—, $C_1$-$C_4$-alkyl-$SO_2$—, where alkyl is preferably methyl or ethyl, halogen (F, Cl, Br, I), nitro, cyano or an —$OSO_2Y$ group, $R^4$, $R^5$ are each, independently of one another, an —N=N—$N(R^2)_2$ group or an —$OSO_2Y$ group, $R^8$ is hydrogen, ethyl, CN, $NO_2$, —$CH_2$—$CH_2$-halogen (F, Cl, Br, I) or $CH_2CH_2OH$, $R^9$, $R^{10}$ are each, independently of one another, hydrogen, hydroxyl, $C_1$-$C_4$-alkyl, $C_1$-$C_4$-alkoxy, where alkyl is preferably methyl or ethyl, halogen (F, Cl, Br, I), nitro, cyano, an —N=N—$N(R^2)_2$ group or an —$OSO_2Y$ group, Y is OH or $N(R^1)_2$, $R^1$ is hydrogen, methyl or ethyl and $R^2$ is methyl or ethyl, with the proviso that, per total molecule (10), one or two —N=N—$N(R^2)_2$ groups and one or two —$OSO_2Y$ groups are located on any ring carbons of aromatic rings, and also their salts, free acids, solvates and the solvates of these salts and the solvates of these free acids.

Preference is given to compounds of the formula (10) in which $R^3$ is hydrogen, hydroxy, methoxy, an —$OSO_2Y$ group, halogen (F, Cl, Br, I), CHO or $CH_2OH$ in the 3 or 4 position, $R^4$ is hydrogen or an —N=N—$N(CH_3)_2$ group in the 3 position, $R^5$ is hydrogen or an —N=N—$N(CH_3)_2$ group in the 3' or 4' position, $R^6$ is hydrogen, hydroxy, methoxy or an —$OSO_2Y$ group in the 3' or 4' position, $R^8$ is hydrogen, ethyl, $CH_2CH_2$ halogen (F, Cl) or $CH_2CH_2OH$, $R^9$, $R^{10}$ are each, independently of one another, hydroxy, methoxy or an —$OSO_2Y$ group in the 3" or 4" position and Y is OH or $NH_2$, with the proviso that, per total molecule (10), one or two —N=N—$N(R^2)_2$ groups and one or two —$OSO_2Y$ groups are located on any ring carbons of aromatic rings, and also their salts, free acids, solvates and the solvates of these salts and the solvates of these free acids.

Particular preference is given to compounds of the formula 10 in which $R^3$ is hydrogen, hydroxy, methoxy or an —$OSO_2Y$ group in the 4 position, $R^4$ is hydrogen or an —N=N—$N(CH_3)_2$ group in the 3 position, $R^5$ is hydrogen or an —N=N—$N(CH_3)_2$ group in the 3' or 4' position, $R^6$ is hydrogen, hydroxy, methoxy or an —$OSO_2Y$ group in the 4' position, $R^8$ is hydrogen or ethyl, $R^9$, $R^{10}$ are each, independently of one another hydroxy, methoxy or an —$OSO_2Y$ group in the 3" or 4" position and Y is OH or $NH_2$, with the proviso that, per total molecule (10), one or two —N=N—$N(CH_3)_2$ groups and one or two —$OSO_2Y$ groups are located on any ring carbons of aromatic rings, and also their salts, free acids, solvates and solvates of these salts and the solvates of these free acids.

As particularly preferred triphenylethylene derivatives (10), mention may be made of the following compounds:

1,1-[bis-3,4"-(disodiosulfooxyphenyl)]-2-ethyl-2-[4'-(3,3-dimethyltriazeno-1)-phenyl]ethene

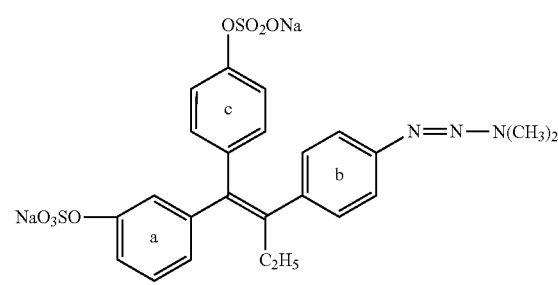

1-(4-hydroxyphenyl)-1-(4''-(sodiosulfooxyphenyl)-2-ethyl-2-[4'-(3,3-dimethyltriazenyl-1)-phenyl]ethene

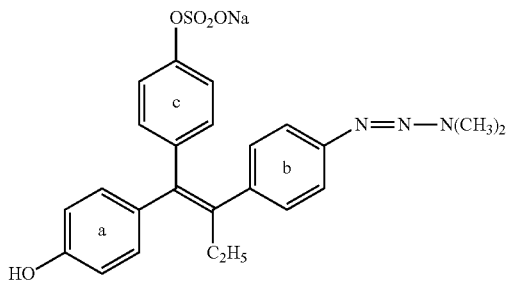

1-[3-(3,3-dimethyltraizenyl-1)-4-methoxyphenyl]-1-(4''-sodiosulfooxyphenyl)-2-ethyl-2-(4'-hydroxyphenyl)ethene

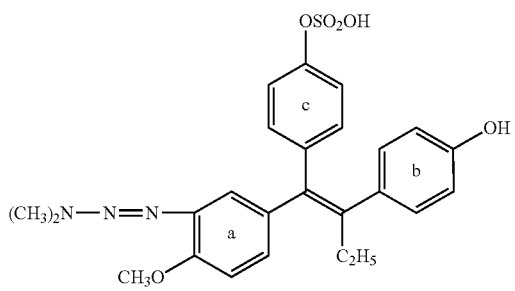

1,1-[bis-4-(sodiosulfooxyphenyl)]-2-ethyl-2-[4'-(3,3-dimethyltriazenyl-1)-phenyl]ethene

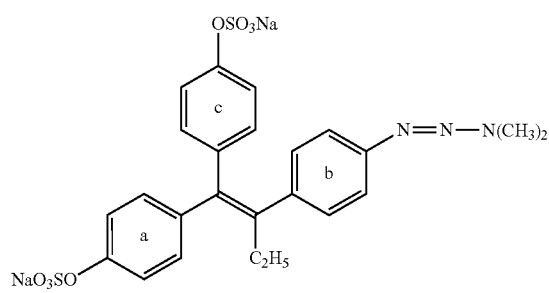

and also their salts, free acids, solvates and the solvates of these salts and the solvates of these free acids.

The compounds (10) can be prepared in a manner analogous to the compounds (1) from the corresponding aromatic amines

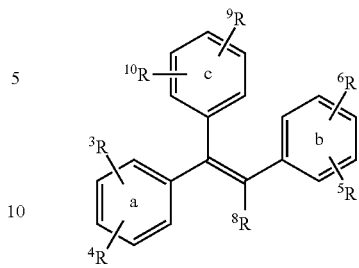

where $R^3$, $R^6$ are each, independently of one another, hydrogen, hydroxyl, $C_1$-$C_4$-alkyl, $C_1$-$C_4$-alkoxy, $C_1$-$C_4$-alkyl-S—, $C_1$-$C_4$-alkyl-SO—, $C_1$-$C_4$-alkyl-$SO_2$—, where alkyl is preferably methyl or ethyl, halogen (F, Cl, Br, I), nitro, cyano or an —$OSO_2Y$ group, $R^4$, $R^5$ are each, independently of one another, an —$NH_2$ group or an —$OSO_2Y$ group, $R^8$ is hydrogen, ethyl, CN, $NO_2$, —$CH_2CH_2$-halogen (F, Cl, Br, I) or $CH_2CH_2OH$, $R^9$, $R^{10}$ are each, independently of one another, hydrogen, hydroxyl, $C_1$-$C_4$-alkyl, $C_1$-$C_4$-alkoxy, where alkyl is preferably methyl or ethyl, halogen (F, Cl, Br, I), nitro, cyano, an —$NH_2$ group or an —$OSO_2Y$ group, Y is OH or $N(R^1)_2$ and $R^1$ is hydrogen, methyl or ethyl, with the proviso that, per total molecule (11), one or two —$NH_2$ groups and one or two —$OSO_2Y$ groups are located on any ring carbons of aromatic rings.

If, for example, 1-(4-aminophenyl)-1-(4''-sodiosulfooxyphenyl)-2-ethyl-2-phenylethene, sodium nitrite and dimethylamine are used as starting materials, the course of the reaction can be represented by the following reaction scheme

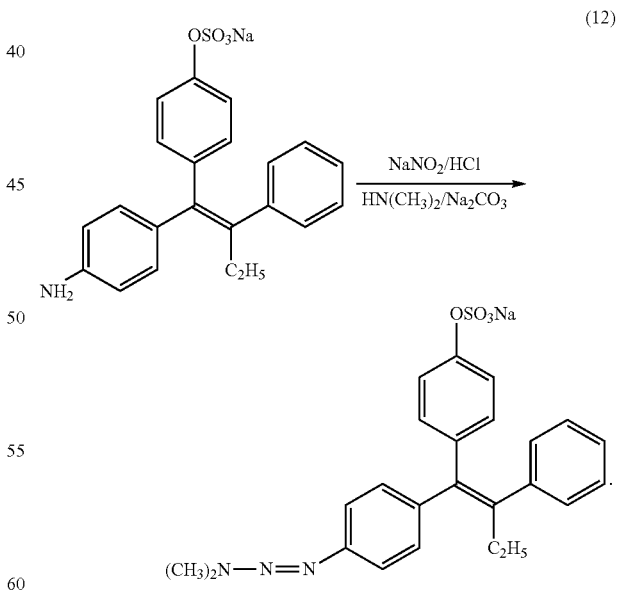

Here, a diazonium salt is prepared in the first step and can be reacted immediately with dimethylamine in a second step to form 1-(4-(3,3-dimethyltriazeno-1-phenyl)-1-(4''-sodiosulfooxyphenyl)-2-ethyl-2-phenylethene.

The aromatic amines (11) can be prepared from the corresponding nitrosulfooxyaromatics or nitrosulfamoyloxyaromatics by generally known methods, e.g. by catalytic reduction by means of hydrogen over palladium/carbon in ethanol or using Ra—Ni in THF.

The triphenylethylene derivatives of the formula (10) can be prepared by the route shown in the reaction scheme (13). Here, the synthesis proceeds according to known methods such as the Wittig reaction, reduction of the nitro group by means of Raney nickel/hydrazine, ether cleavage, preparation of the triazenylphenol and reaction of this with alkali metal bisulfate or sulfamoyl chloride. Instead of alkali metal bisulfate in DMF, it is also possible to use chlorosulfonic acid in pyridine.

$R^4$, $R^5$ are each, independently of one another, an —N=N—N($R^2$)$_2$ group or an —OSO$_2$Y group,
Y is OH or N($R^1$)$_2$,
$R^1$ is hydrogen, methyl or ethyl and
$R^2$ is methyl or ethyl,
with the proviso that, per total molecule (14), one or two —N=N—N($R^2$)$_2$ groups and one or two —OSO$_2$Y groups are located on any ring carbons of aromatic rings,
and also their salts, free acids, solvates and the solvates of these salts and the solvates of these free acids.

Preference is given to compounds of the formula (14) in which

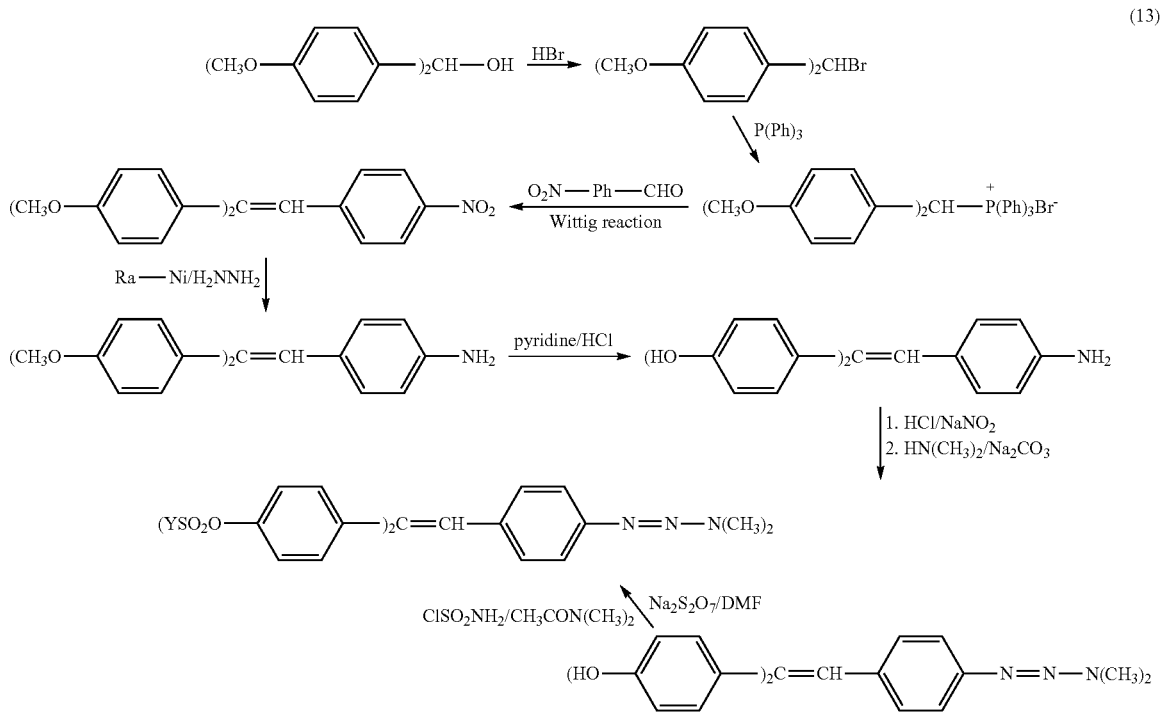

(13)

3. Isoflavones of the Formula (14)

When, in formula (1),

X is a divalent —C(O)—C*=CH—O— radical which together with the two adjacent carbon atoms of the ring a on which it is located forms a pyranone ring, where the ring b is located on the C* atom of this radical, formula (I) becomes the formula

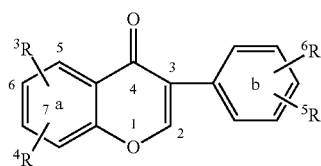

(14)

where $R^3$, $R^6$ are each, independently of one another, hydrogen, hydroxyl, $C_1$-$C_4$-alkyl, $C_1$-$C_4$-alkoxy, $C_1$-$C_4$-alkyl-S—, $C_1$-$C_4$-alkyl-SO—, $C_1$-$C_4$-alkyl-SO$_2$—, where alkyl is preferably methyl or ethyl, halogen (F, Cl, Br, I), nitro, cyano or an —OSO$_2$Y group $R^3$, $R^6$ are each, independently of one another, hydroxy, methoxy or an —OSO$_2$Y group,
$R^4$, $R^5$ are each, independently of one another, hydrogen, hydroxy, methoxy or an —N=N—N(CH$_3$)$_2$ group and
Y is OH or NH$_2$,
with the proviso that, per total molecule (14), one or two —N=N—N(CH$_3$)$_2$ groups and one or two —OSO$_2$Y groups are located on any ring carbons of aromatic rings,
and also their salts, free acids, solvates and the solvates of these salts and the solvates of these free acids.

Particular preference is given to compounds of the formula (14) in which $R^3$ is hydroxy, methoxy or an —OSO$_2$Y group in the 5 or 7 position,
$R^4$ is hydrogen or an —N=N—N(CH$_3$)$_2$ group in the 6 position,
$R^5$ is hydroxy, methoxy or an —OSO$_2$Y group in the 4' position,
$R^6$ is an —N=N—N(CH$_3$)$_2$ group in the 2' or 3' position and
Y is OH or NH$_2$,
with the proviso that, per total molecule (14), one or two —N=N—N(CH$_3$)$_2$ groups and one or two —OSO$_2$Y groups are located on any ring carbons of aromatic rings,
and also their salts, free acids, solvates and the solvates of these salts and the solvates of these free acids.

As particularly preferred isoflavones (14), mention may be made of the following compounds:

7-hydroxy-3-[3'-(3,3-dimethyltriazenyl-1)-4'-sodio-sulfooxy]isoflavone

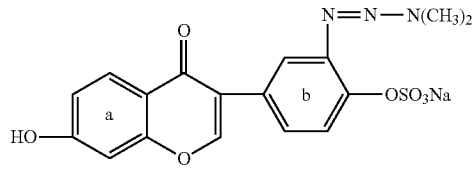

6-(3,3-dimethyltriazenyl-1)-7-methoxy-3-(4'-sodio-sulfooxy)isoflavone

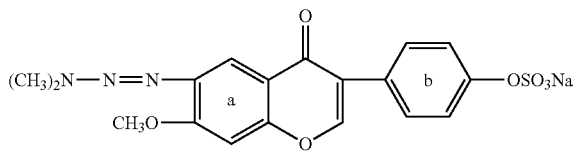

7-methoxy-3'-(3,3-dimethyltriazenyl-1)-4'-sodiosul-fooxyisoflavone

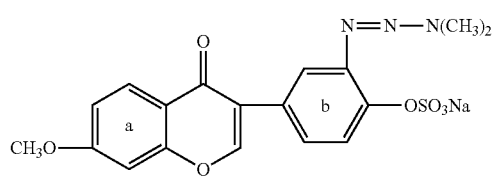

7-sodiosulfooxy-2'-(3,3-dimethyltriazenyl-1)-4'-sul-famoyloxyisoflavone

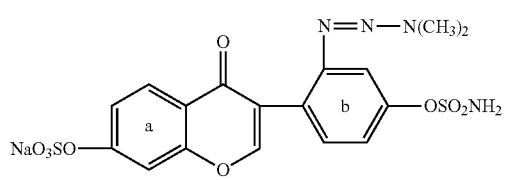

and also their salts, free acids, solvates and the solvates of these salts and the solvates of these free acids.

The isoflavones (3) according to the invention can be prepared in a manner analogous to the compounds (1) from the corresponding aromatic amines

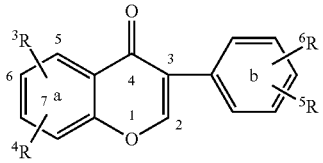

(15)

where
R$^3$, R$^6$ are each, independently of one another, hydrogen, hydroxyl, C$_1$-C$_4$-alkyl, C$_1$-C$_4$-alkoxy, C$_1$-C$_4$-alkyl-S—, C$_1$-C$_4$-alkyl-SO—, C$_1$-C$_4$-alkyl-SO$_2$—, where alkyl is preferably methyl or ethyl, halogen (F, Cl, Br, I), nitro, cyano or an —OSO$_2$Y group,
R$^4$, R$^5$ are each, independently of one another, an —NH$_2$ group or an —OSO$_2$Y group,
Y is OH or N(R$^1$)$_2$ and
R$^1$ is hydrogen, methyl or ethyl,
with the proviso that, per total molecule (15), one or two —NH$_2$ groups and one or two —OSO$_2$Y groups are located on any ring carbons of aromatic rings.

If, for example, 6-amino-7,4'-dipotassiosulfooxyisoflavone, sodium nitrite and dimethylamine are used as starting materials, the course of the reaction can be represented by the following reaction scheme.

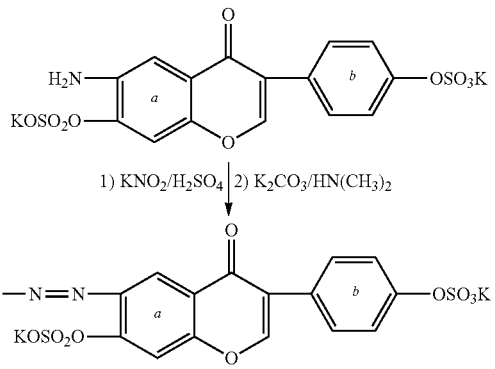

(16)

Here, a diazonium salt is prepared in the first step and reacts immediately with dimethylamine in a second step to form the 7,4'-dipotassiosulfooxy-6-(3,3-dimethyltriazenyl-1)-isoflavone according to the invention.

The previously unknown aromatic amines (15) can be prepared from the corresponding nitrosulfooxyaromatics or nitrosulfamoyloxyaromatics by methods known to any person skilled in the art, e.g. by catalytic reduction by means of hydrogen over palladium/carbon in ethanol or Ra—Ni in THF.

[0] The nitroisoflavones of the type used as starting material in the reaction scheme (17) below are known and can be prepared by known methods (Z. Kristallogr. NCS 222, 293-294 (2007)).

The preparation of the new starting materials having sulfooxy or sulfamoyloxy groups can be carried out by reaction of the corresponding aromatic phenols with chlorosulfonic acid in pyridine or with alkaline metal bisulfate in DMF or with sulfamoyl chlorides in dimethylacetamide. The individual reaction steps are illustrated in the reaction scheme (17):

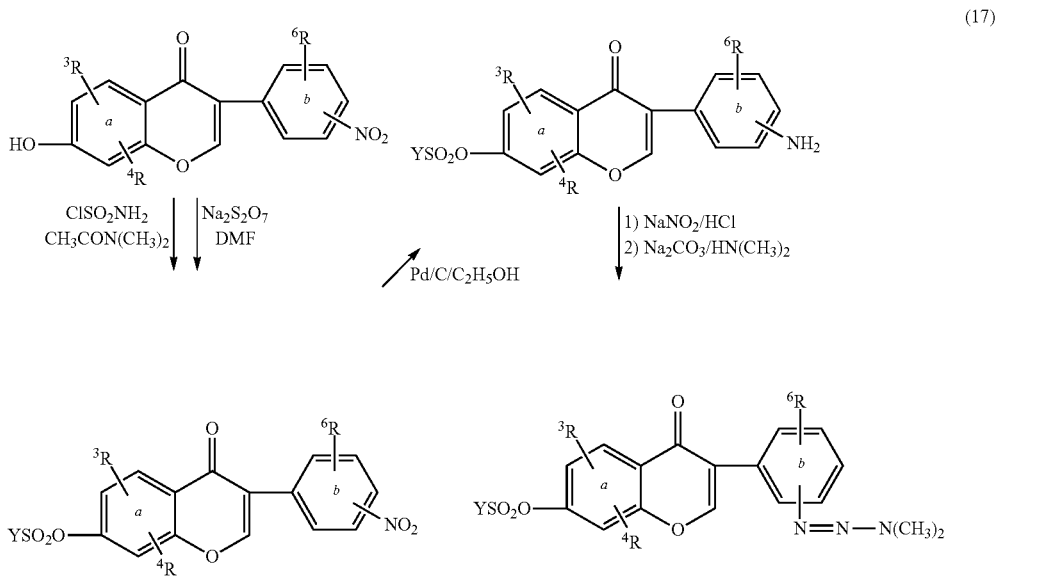

(17)

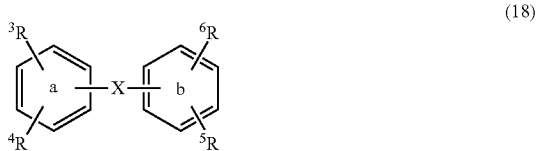

4. Diphenyl Derivatives of the Formula (18) Which are Either Unbridged or Bridged by Atoms or Diatomic Groups:

According to the invention, formula (I) can also be in the form of the formula (18)

where

X is a direct C—C bond, $CH_2$, CHOH, CO, S, SO, $SO_2$ or —N=N—, $R^3$, $R^6$ are each, independently of one another, hydrogen, hydroxyl, $C_1$-$C_4$-alkyl, $C_1$-$C_1$-alkoxy, $C_1$-$C_4$-alkyl-S—, $C_1$-$C_4$-alky-SO—, $C_1$-$C_4$-alkyl-$SO_2$—, where alkyl is preferably methyl or ethyl, halogen (F, Cl, Br, I), nitro, cyano or an —$OSO_2Y$ group, $R^4$, $R^5$ are each, independently of one another, an —N=N—N($R^2$)$_2$ group or an —$OSO_2Y$ group, Y is OH or N($R^1$)$_2$, $R^1$ is hydrogen, methyl or ethyl and $R^2$ is methyl or ethyl, with the proviso that, per total molecule (18), one or two —N=N—N($R^2$)$_2$ groups and one or two —$OSO_2Y$ groups are located on any ring carbons of aromatic rings, and also their salts, free acids, solvates and the solvates of these salts and the solvates of these free acids.

Preference is given to compounds of the formula (18) in which

X is $CH^2$, CO, SO or $SO_2$, $R^3$, $R^6$ are each, independently of one another, hydrogen, hydroxy, methyl, ethyl, methoxy, $CH_3S$—, $CH_3SO$—, $CH_3SO_2$—, halogen (F, Cl, Br, I), nitro, cyano or the —$OSO_2Y$ group, $R^4$, $R^5$ are each, independently of one another, an —N=N—N($CH_2$)$_2$ group or an —$OSO_2Y$ group and Y is OH or $NH_2$, with the proviso that, per total molecule (18), one or two —N=N—N($CH_2$)$_2$ groups and one or two —$OSO_2Y$ groups are located on any ring carbons of aromatic rings, and also their salts, free acids, solvates and the solvates of these salts and the solvates of these free acids.

Particular preference is given to compounds of the formula (18) in which

X is $CH_2$, CO, SO or $SO_2$, $R^3$, $R^6$ are each, independently of one another, hydrogen, hydroxy, methyl, fluorine, chlorine, bromine or an —$OSO_2Y$ group, $R^4$ is hydrogen, $R^5$ is a $(CH_2)_2$N—N=N group and Y is OH or $NH_2$, with the proviso that, per total molecule (18), one or two —N=N—N($CH_2$)$_2$ groups and one or two —$OSO_2Y$ groups are located on any ring carbons of aromatic rings, and also their salts, free acids, solvates and the solvates of these salts and the solvates of these free acids.

Very particular preference is given to compounds of the formula (18) in which

X is $CH_2$, CO, SO or $SO_2$, $R^3$ is hydroxy, methyl, chlorine or bromine in the 2, 3 or 4 position, $R^4$ is the —$OSO_2Y$ group in the 2, 3 or 4 position, $R^5$ is a $(CH_2)_2$N—N=N group in the 4' position, $R^6$ is hydrogen, methyl, fluorine, chlorine or bromine in the 2', 3' or 5' position and Y is OH or $NH_2$, with the proviso that, per total molecule (18), one or two —N=N—N($CH_3$)$_2$ groups and one or two —$OSO_2Y$ groups are located on any ring carbons of aromatic rings, and also their salts, free acids, solvates and the solvates of these salts and the solvates of these free acids.

The most preferred diphenyl derivatives bridged by diatomic or triatomic groups include the following compounds:

21

4-(3,3-dimethyltriazenyl-1)-4'-hydroxy-2'-sodiosulfooxybenzophenone

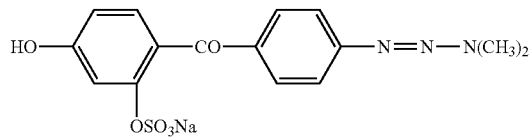

4-(3,3-dimethyltriazenyl-1)-4'-hydroxy-3'-sodiosulfooxybenzophenone

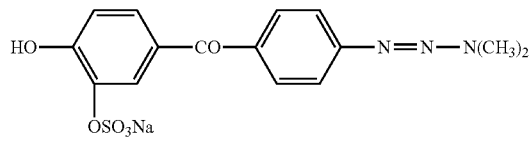

4-(3,3-dimethyltriazenyl-1)-3'-hydroxy-4'-sodiosulfooxybenzophenone

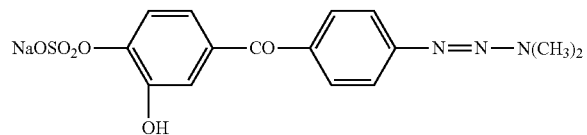

4-(3,3-dimethyltriazenyl-1)-4'-sodiosulfooxy-3'-sulfamoyloxybenzophenone

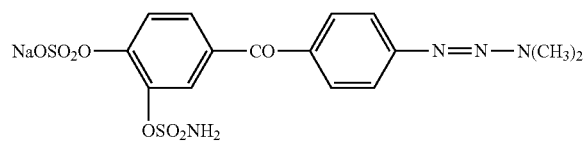

4-(3,3-dimethyltriazenyl-1)-4'-sodiosulfooxydiphenylmethane

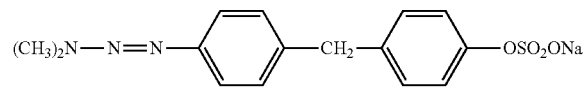

22

2-chloro-4-(3,3-dimethyltriazenyl-1)-4'-sodiosulfooxy(diphenyl sulfone)

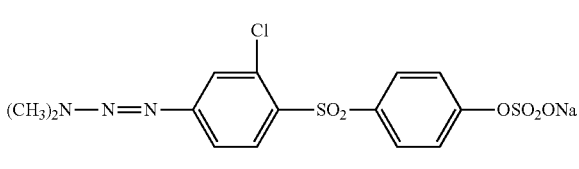

and also their salts, free acids, solvates and the solvates of these salts and the solvates of these free acids.

Particular preference is given to 4-(3,3-dimethyltriazenyl-1)-4'-sodiosulfooxybenzophenone

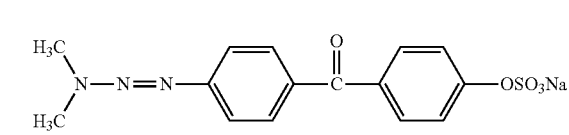

The starting materials for the synthesis of the compounds (18) are known and can be prepared by the processes described in GB 1 371 969 and utilized for the synthesis of the compounds (18) by converting the hydroxytriazene derivatives of the type (19) described there into end products, e.g. (20), as is shown by way of example in the reaction scheme (21).

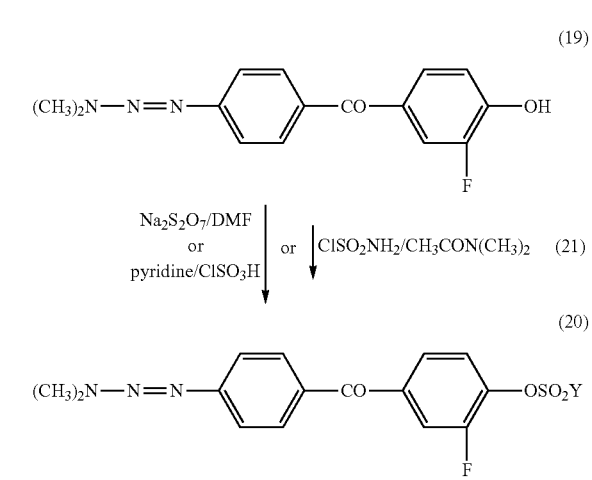

where Y has the meaning indicated in the legends for formula (18).

The present invention further provides diphenyl derivatives containing (i) at least one dialkyltriazenyl group and (ii) at least one sulfooxy group and/or at least one sulfomoyloxy group per molecule and their salts, solvates and solvates of these salts for use as medicaments and also the use of these compounds for producing medicaments, preferably for the treatment of cancers of the tissues dependent on estrogens, in particular of estrogen receptor-negative and estrogen receptor-positive tumors of the sex organs, and of a melanoma.

In a preferred embodiment of the present invention, the substituted diphenyl derivatives of the invention can be used in combination with monoclonal antibodies.

According to the present invention, preference is given to using monoclonal antibodies which have a high selectivity in the tumor cell (Discovery Medicine, Alain Beck, "The next generation of Antibody-drug Conjugates Comes of Age", Oct. 16, 2010).

The substituted diphenyl derivatives of the invention are bound to the monoclonal antibody and introduced into the tumor cell.

In general, the diphenyl derivatives of the invention and the monoclonal antibodies are used in a ratio of from 0.5:1 (diphenyl derivative to antibody) to 4:1.

Monoclonal antibodies are known per se. Monoclonal antibodies are immunologically active proteins which are produced from a cell line going back to a single B-lymphocyte and are directed against a single epitope (e.g. a tumor cell).

The compounds of the invention can, for example, be used for the treatment of the following types of tumor: breast cancer (mamma carcinoma), cancer of the uterus (endometrium carcinoma, corpus carcinoma), cervical cancer, ovarian cancer (ovarian carcinoma), vaginal cancer, prostate cancer, skin cancer, melanoma (maligna melanoma).

The invention further provides for the use of the compounds of the invention in combination with at least one further chemotherapeutic agent for the treatment of cancer. The compounds of the invention can accordingly also be used in combination with further chemotherapeutic agents known in the treatment of cancer or tumors and/or with medicaments which are administered together with the chemotherapeutic agents during chemotherapy.

Examples of such chemotherapeutic agents which can be used in combination with other medicaments used in chemotherapy are described, for example, in WO/2007/061978 under the key words "Combination Therapy" (page 23, line 1 to page 30, line 18) or in US 2007/135424 A1 (paragraphs 153 to 171).

For these methods of administration, the active compound can be administered in suitable administration forms. For oral administration, known administration forms which release the active compound quickly and/or in modified form, e.g. tablets (uncoated and coated tablets, e.g. tablets provided with coatings resistant to stomach juices or film tablets), capsules, dragees, granules, pellets, powders, emulsions, suspensions, solutions and aerosols are suitable.

Parenteral administration can occur with circumvention of a resorption step (intravenous, intraarterial, intracardial, intraspinal or intralumbal) or with involvement of resorption (intramuscular, subcutaneous, intracutaneous, percutaneous or intraperitoneal). Administration forms suitable for parenteral administration are, inter alia, injection and infusion preparations in the form of solutions, suspensions, emulsions, lyophilizates and sterile powders.

For the other administration methods, suitable forms are, for example, inhalation medicaments (including powder inhalers, nebulizers), nose drops/solutions, sprays; tablets or capsules to be administered lingually, sublingually or buccally, suppositories, ear and eye preparations, pessaries, aqueous suspensions (lotions, mixtures to be shaken), lipophilic suspensions, ointments, creams, milk, pastes, powder to be sprinkled or implants.

The active compounds can be converted in a manner known per se into the administration forms described. This can be effected using inert, nontoxic, pharmaceutically suitable auxiliaries. These include, inter alia, supports (e.g. microcrystalline cellulose), solvents (e.g. liquid polyethylene glycols), emulsifiers (e.g. sodium dodecyl sulfate), dispersants (e.g. polyvinylpyrrolidone), synthetic and natural biopolymers (e.g. albumin), stabilizers (e.g. antioxidants such as ascorbic acid), colorants (e.g. inorganic pigments such as iron oxides) or flavors and/or fragrances.

In general, it is advisable in the case of parenteral administration, to administer amounts of from about 1 to 40 mg/kg, preferably from about 2.5 to 15 mg/kg, of body weight in order to achieve effective results. In the case of oral administration, the amount is from about 1 to 70 mg/kg, preferably from about 1 to 50 mg/kg, of body weight.

It may nevertheless be necessary to deviate from the abovementioned amounts depending on body weight, method of administration, individual response to the active compound, type of preparation and point in time or interval at which administration occurs. Thus, it can in some cases be sufficient to employ less than the abovementioned minimum amount, while in other cases the abovementioned upper limit has to be exceeded. In the case of administration of relatively large amounts, it can be advisable to distribute these as a plurality of individual doses over the day.

The present invention further provides pharmaceutical compositions containing at least one of the compounds according to the invention together with at least one pharmacologically acceptable carrier, auxiliary or solvent. These are conventional pharmaceutical carriers, auxiliaries or solvents. The pharmaceutical compositions of the invention are, for example, suitable for inhalation or intravenous, intraperitoneal, intramuscular, intravaginal, intrabuccal, percutaneous, subcutaneous, mucocutaneous, oral, rectal, transdermal, topical, intradermal, intragastral or intracutaneous administration and are, for example, present in the form of pills, tablets, tablets which are resistant to stomach juices, film tablets, coated tablets, retard formulations for oral, subcutaneous or cutaneous administration (in particular as adhesive plasters), depot formulations, dragees, plugs, gels, ointments, syrup, inhalation powders, granules, suppositories, emulsions, dispersions, microcapsules, microformulations, nanoformulations, liposomal formulations, capsules, capsules resistant to stomach juices, powders, inhalation powders, microcrystalline formulations, inhalation sprays, dusts, drops, nose drops, nose sprays, aerosols, ampoules, solutions, juices, suspensions, emulsions, infusion solutions or injection solutions, etc.

EXAMPLES

The percentages in the following examples are, unless indicated otherwise, percentages by weight; parts are parts by weight. Solvent ratios, dilution ratios and concentrations of liquid/liquid solutions are in each case by volume.

1. Stilbene Derivatives of the Formula (5)
Starting Materials

Example 1.1

2-sodiosulfooxybenzaldehyde

The following method can serve as pattern for sulfation by means of alkali metal bisulfates

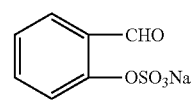

12.2 g (0.1 mol) of 2-hydroxybenzaldehyde and 33.3 g (0.15 mol) of sodium disulfate are admixed with 100 ml of dimethylformamide and 130 ml of tetrahydrofuran and stirred at room temperature for 30 hours. 200 ml of a 1 N aqueous sodium carbonate solution is then added to the reaction mixture, the mixture is stirred, filtered and the filtrate is evaporated under reduced pressure. The residue is dissolved in the minimum amount of water needed, filtered through activated carbon and the filtrate is evaporated on a rotary evaporator. The title substance can be processed further as crude product.

Example 1.2

4-sodiosulfooxybenzaldehyde

The compound is prepared in a manner analogous to example 1.1 and the crude product is processed further.

3-Sodiosulfooxybenzaldehyde can be obtained in an analogous way

Example 1.3

2-sulfamoyloxybenzaldehyde

The method below serves as pattern for sulfamylation using sulfamoyl chloride.

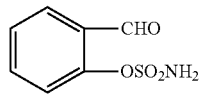

12.46 g (0.11 mol) of sulfamoyl chloride are added dropwise to a solution of 12.2 g (0.1 mol) of 2-hydroxybenzaldehyde in 200 ml of anhydrous dimethylacetamide at from 0 to 5° C. The reaction mixture is stirred at room temperature for 3 hours and then extracted with 1000 ml of ethyl acetate, the organic phase is washed with a saturated aqueous sodium hydrogencarbonate solution, dried over sodium sulfate and the solvent is taken off on a rotary evaporator. The residue is triturated with a mixture of ethyl acetate/petroleum ether, crystallized and filtered off with suction.

Example 1.4

4-sulfamoyloxybenzaldehyde

Synthesis Analogous to Example 1.3

The 3-sulfamoyloxy derivatives of 3-hydroxybenzaldehyde can be obtained in an analogous way.

Example 1.5

(4-nitrobenzyl)triphenylphosphonium chloride

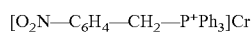

A solution of 263 g (1 mol) of triphenylphosphine and 172 g (1 mol) of 4-nitrobenzyl chloride in 2 l of toluene is stirred at the boiling point for 15 hours. The reaction mixture is cooled, the crystals are filtered off with suction and washed with toluene.

Example 1.6

(Z- and E)-2-sodiosulfooxy-4'-nitrostilbene

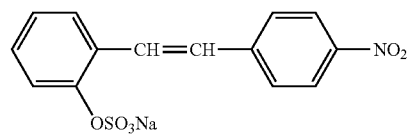

0.04 mol of sodium methoxide (in methanolic solution) and a solution of 17.3 g of phosphonium salt (from example 1.5) in 40 ml of methanol are simultaneously added dropwise in small portions to a solution of 8.9 g (0.04 mol) of sodium benzaldehyde-2-sulfate in 50 ml of methanol at 0° C. while stirring. After decoloration of the reaction solution, the solvent is distilled off on a rotary evaporator. The solid product is extracted with 100 ml of ethyl acetate while stirring in order to remove the triphenylphosphine oxide, filtered off with suction, dried in air, then boiled with nitromethane and separated from the insoluble residue (trans compound) by filtration with suction. On cooling, the cis compound crystallizes out from the filtrate and is optionally recrystallized once more.

Example 1.7

(Z- and E)-4-methoxy-2-sodiosulfooxy-4'-nitrostilbene

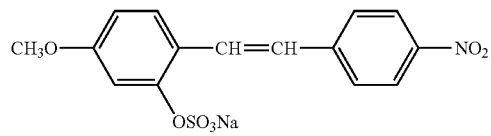

Synthesis Analogous to Example 1.6

Example 1.8

(Z- and E)-4-nitro-2'-sulfamoyloxystilbene

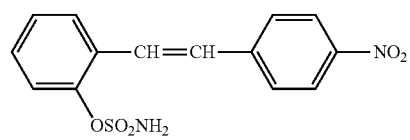

At 0 to 5° C., 13.15 g (0.05 mol) of phosphonium salt from example 1.5 and 0.05 mol of sodium methoxide solution are simultaneously added a little at a time (after decoloration in each case) to a solution composed of 10.4 g (0.05 mol) of aldehyde from example 1.3 and 75 ml of ethanol. After decoloration of the reaction solution, the solvent is taken off on a rotary evaporator and the residue is stirred with 50 ml of toluene to remove the triphenylphosphine and filtered off with suction. The residue which remains is heated with 75 ml of acetonitrile and filtered off with suction while hot. The trans compound remains. The cis compound crystallizes out from acetonitrile under refrigeration and can optionally be recrystallized from acetonitrile or isopropanol.

Example 1.9

(Z)-4-amino-(2-sodiosulfooxy)stilbene

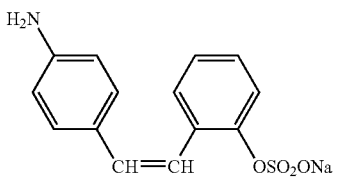

3.4 g (0.01 mol) of Z-nitro compound from example 1.8 are hydrogenated in 300 ml of methanol or THF and 20 ml of water using 4 g of Ra—Ni at room temperature and 2 atm. After the required amount of hydrogen has been taken up, the catalyst is filtered off with suction and the solvent is distilled off. The residue is reacted further as crude product.

The following amino compounds are obtained analogously:

Example 1.10

(E)-4-amino-2'-sodiosulfooxystilbene (from example 1.6 E)

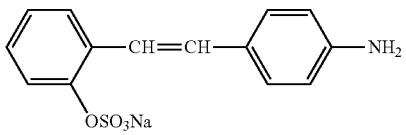

Example 1.11

(Z)-4-amino-2'-sulfamoyloxystilbene (from example 1.8 Z)

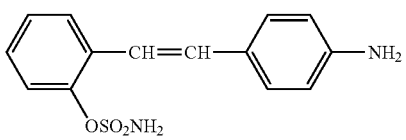

Example 1.12

(E)-4-amino-2'-sulfamoyloxystilbene (from example 1.8 E)

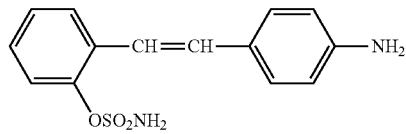

End Products

Example 1.13

(Z)-4-(3,3-dimethyltriazenyl-1)-2'-sodiosulfooxystilbene

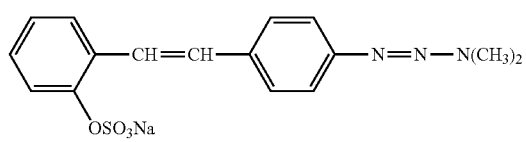

A solution composed of 3.5 g of sodium nitrite and 5 ml of water is added dropwise to a solution composed of 15.6 g (0.05 mol) of cis-aminostilbene from example 1.9, 100 ml of water and 13 ml of conc. hydrochloric acid at 0° C. and the mixture is stirred for another 10 minutes. The resulting diazonium salt solution is then quickly added dropwise to a solution composed of 30 g of sodium carbonate, 60 ml of water and 7 g of 40% strength aqueous dimethylamine solution. The mixture is stirred for another 40 minutes and the reaction solution is evaporated on a rotary evaporator. The residue is dissolved in the minimum amount of water needed at 50° C. and the title compound is precipitated by means of a saturated aqueous sodium chloride solution, filtered off with suction and dried. The product can be recrystallized from a sodium chloride solution or from methanol/water.

The following compound is prepared in an analogous way:

Example 1.14

(E)-4-(3,3-dimethyltriazenyl-1)-2'-sodiosulfooxystilbene

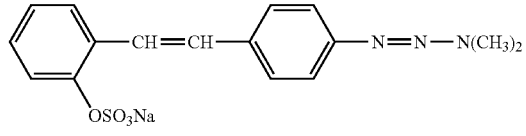

(from example 1.10 in an analogous way to example 1.13)

Example 1.15

(Z)-4-(3,3-dimethyltriazenyl-1)-2'-sulfamoyloxystilbene

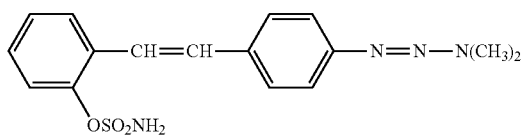

A solution composed of 3.5 g of sodium nitrite and 5 ml of water is added dropwise to a solution composed of 15.6 g (0.05 mol) of Z-aminostilbene from example 1.11, 100 ml of water and 10 ml of conc. hydrochloric acid at 0° C. and the mixture is stirred for another 10 minutes. The resulting diazonium salt solution is then quickly added dropwise to a solution composed of 30 g of sodium carbonate, 60 ml of water and 7 g of 40% strength aqueous dimethylamine solution. The mixture is stirred for another 40 minutes, 50 ml of water are added and the mixture is extracted with 300 ml of ethyl acetate. The organic phase is separated off, washed with 300 ml of a saturated aqueous sodium hydrogencarbonate solution, dried over sodium sulfate and evaporated. The product is purified by chromatography and then optionally recrystallized from ethanol/cyclohexane.

Example 1.16

(E)-4-(3,3-dimethyltriazenyl-1)-2'-sulfamoyloxystilbene (from example 1.12)

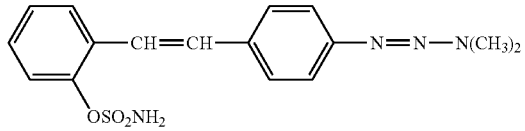

2. Triphenylethylene Derivatives of the Formula (12) Starting Materials

Example 2.1

[bis(4-methoxyphenyl)]bromomethane $(CH_3O-C_6H_4-)_2CH-Br$

Hydrogen bromide is passed into a suspension of 100 g of bis(4-methoxyphenyl)carbinol and 46 g of calcium chloride in 2 l of toluene to saturation. The precipitated salt is filtered off with suction and the filtrate is evaporated. The yellow oily residue is processed further in crude form.

Example 2.2

[bis(4-methoxyphenyl)methyl]triphenylphosphonium bromide

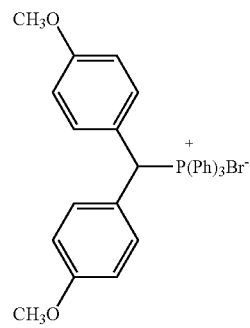

The title compound is prepared from the bromide of example 2.1 in an analogous way to example 1.5.

Example 2.3

1,1-[bis(4-methoxyphenyl)]-2-(4-nitro-phenyl)ethene

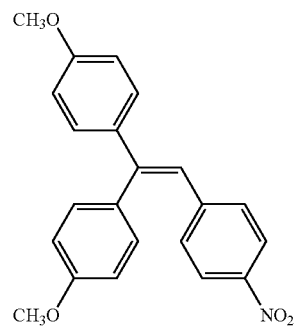

4.5 g (0.1 mol) of sodium hydride (53% strength dispersion in oil) are introduced under absolutely dry conditions into 50 ml of DMSO. The mixture is heated to 70-80° C. until evolution of hydrogen stops. While cooling in ice, 57 g (0.1 mol) of the phosphonium salt from example 2.2 dissolved in 150 ml of DMSO are added dropwise and the mixture is stirred for another 1 hour. 15.1 g (0.1 mol) of 4-nitrobenzaldehyde dissolved in 50 ml of DMSO are subsequently added dropwise and the mixture is stirred at room temperature for another 15 hours. 600 ml of water are then added, the mixture is extracted with 500 ml of ethyl acetate, the solvent is removed on a rotary evaporator and the product is separated off from the triphenylphosphine oxide via an aluminum oxide column. Toluene/ethyl acetate (9:1) is used as eluant. The second fraction is freed of the solvent on a rotary evaporator and processed further as crude product.

Example 2.4

1,1-[bis(4-methoxyphenyl)]-2-(4-aminophenyl)ethene

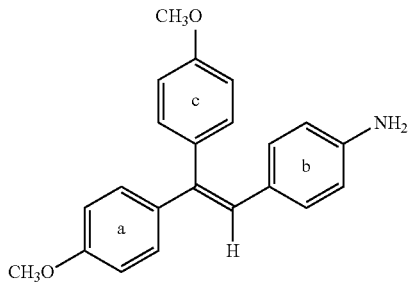

15.26 g (0.042 mol) of the nitro compound from example 2.4 are heated to boiling in 500 ml of ethanol, admixed with 66 g of an 80% hydrazine hydrate solution (1.06 mol of $N_2H_4$) and rapidly cooled to 50° C. and then admixed while stirring with freshly prepared Raney nickel suspended in a neutral ethanol medium until no further evolution of gas is observed when more catalyst is added. The mixture is subsequently heated under reflux for another 1 hour and the hot reaction mixture is filtered. After washing the residue on the filter with 250 ml of hot ethanol, the combined filtrates are evaporated to dryness under reduced pressure and the residue is optionally recrystallized from ethanol.

Example 2.5

1,1-[bis(4-hydroxyphenyl)]-2-(4-amino-phenyl)ethane

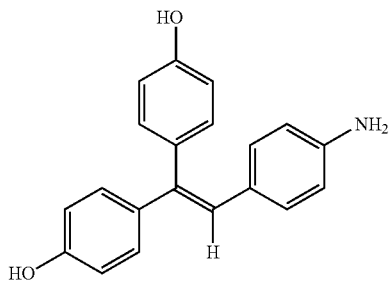 [SMILES: Nc1ccc(C=C(c2ccc(O)cc2)c2ccc(O)cc2)cc1]

84 g of conc. hydrochloric acid are added dropwise to a mixture of 33 g (0.1 mol) of the compound of example 2.4 and 66 ml of pyridine. The reaction solution is then heated at 150° C. for 3 hours and subsequently evaporated to dryness on a rotary evaporator, taken up in 200 ml of water and neutralized. The solid reaction product is filtered off with suction and dried. The crude product is reacted further.

Example 2.6

1,1-[bis(4-hydroxyphenyl)]-2-[4-(3,3-dimethyltriazenyl-1)phenyl]ethene

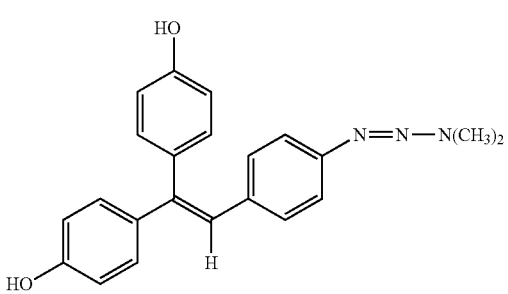 [SMILES: CN(C)N=Nc1ccc(C=C(c2ccc(O)cc2)c2ccc(O)cc2)cc1]

13.55 g (0.05 mol) of 1,1-[bis(4-hydroxyphenyl)]-2-(4-aminophenyl)ethene from example 2.5 are dissolved in a solution composed of 13 ml of concentrated hydrochloric acid and 80 ml of water. A solution composed of 10 ml of water and 3.5 g of sodium nitrite are slowly added dropwise thereto at from 0 to 5° C. while stirring. The resulting diazonium salt solution is then quickly added dropwise at from 0 to 5° C. to a solution composed of 15 g of sodium carbonate, 60 ml of water and 7 g of 40% strength aqueous dimethylamine solution. The mixture is subsequently stirred for another 30 minutes, neutralized and the title substance is filtered off with suction as a solid, optionally recrystallized from nitropropane and dried. The crude product is processed further.

End Products

Example 2.7

1,1-[bis-4-(sodiosulfooxyphenyl)]-2-[4-(3,3-dimethyltriazenyl-1)phenyl]ethene

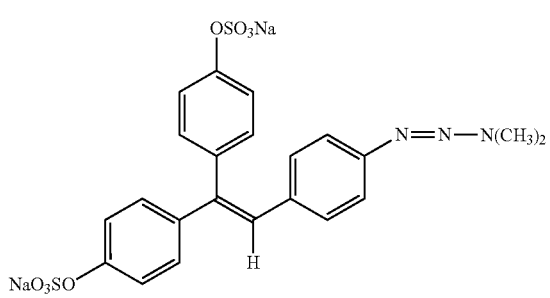

3.60 g (0.01 mol) of the compound from example 2.6 and 6.6 g (0.03 mol) of sodium bisulfate are admixed with 10 ml of dimethylformamide and 13 ml of tetrahydrofuran and stirred at room temperature for 30 hours. 20 ml of a 1 N aqueous sodium carbonate solution is then added to the reaction mixture, the mixture is stirred, the solid is filtered off with suction and the filtrate is evaporated under reduced pressure. The residue is dissolved in the minimum amount of water needed, filtered through activated carbon, the filtrate is evaporated on a rotary evaporator and the residue is recrystallized from methanol/water.

Example 2.8

1,1-[bis-4-(sulfamoyloxyphenyl)]-2-[4-(3,3-dimethyltriazenyl-1)-phenyl]ethene

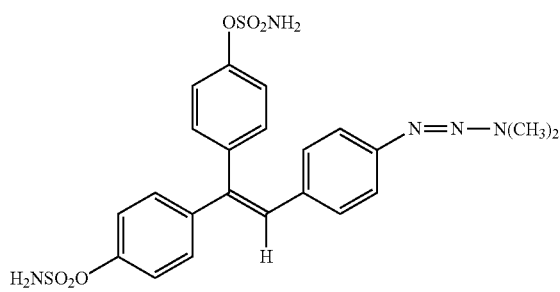

4 g (0.033 mol) of sulfamoyl chloride are added dropwise to a solution of 3.60 g (0.01 mol) of the compound from example 2.6 in 20 ml of anhydrous dimethylacetamide at from 0 to 5° C. The reaction mixture is stirred at room temperature for 3 hours. The mixture is then extracted with 100 ml of ethyl acetate, the organic phase is washed with a saturated aqueous sodium hydrogencarbonate solution, dried over sodium sulfate and the solvent is distilled off on a rotary evaporator. The residue is triturated with an ethyl acetate/petroleum ether mixture, induced to crystallize and filtered off with suction.

3. Flavonoid Derivatives of the Formula (14)
Starting Materials

Example 3.1

7,4'-dihydroxy-3'-nitroisoflavone

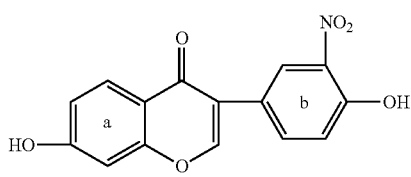

20 ml of a mixture of concentrated sulfuric acid and nitric acid (3:1) are added dropwise to a solution of 1 g of daidzein in 200 ml of dry ethanol at room temperature while stirring vigorously. The mixture is stirred for another 2 hours, and 400 ml of water are then added. The compound precipitates, is filtered off with suction and washed with water until neutral. The yellow product is recrystallized from alcohol.

The 2'-nitrisoflavones are obtained according to the electronic thesis of S. Tappmeyer: http://www.diss.fu-berlin.de/2004/287/index.html.

Synthesis of the Sulfates

The following examples are carried out in a manner analogous to example 1.1. The title compounds are reacted further as crude products.

Example 3.2

7-sodiosulfooxy-4'-methoxy-2'-nitroisoflavone

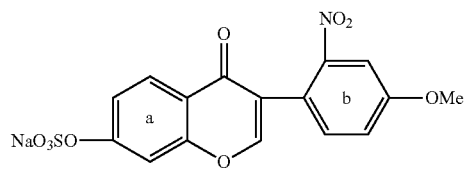

Example 3.3

7,4'-disodiosulfooxy-2'-nitroisoflavone

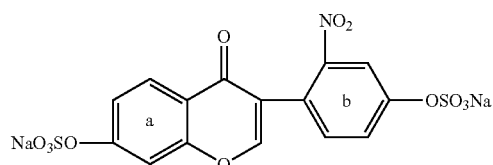

Example 3.4

7,4'-disodiosulfooxy-3'-nitroisoflavone

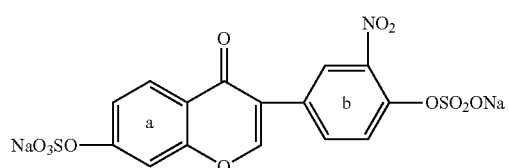

Example 3.5

7-methoxy-3'-nitro-4'-sodiosulfooxyisoflavone

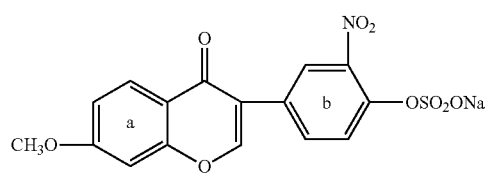

Example 3.6

7-sodiosulfooxy-3'-nitro-4'-methoxyisoflavone

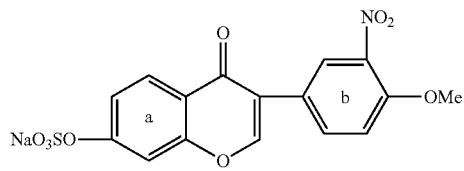

Synthesis of the Oxysulfamates

The following examples are carried out in a manner analogous to example 1.3. The title compounds are reacted further as crude products.

Example 3.7

7,4'-disulfamoyloxy-2'-nitroisoflavone

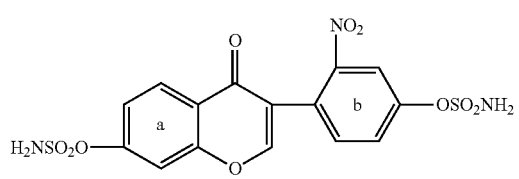

Example 3.8

7,4'-disulfamoyloxy-3'-nitroisoflavone

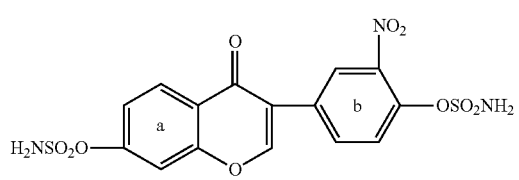

Reduction of the Nitroisoflavones to the Aminoisoflavones

The reduction of the nitro compounds is carried out by catalytic reduction using hydrogen/Pd/C in ethanol.

Example 3.9

7-sodiosulfooxy-2'-amino-4'-methoxyisoflavone

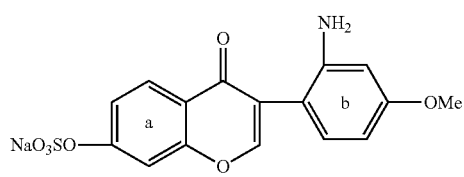

The following are prepared in an analogous way:

Example 3.10

7,4'-disodiosulfooxy-2'-aminoisoflavone

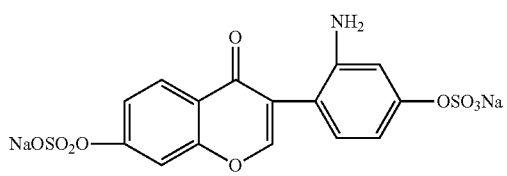

3.11 7,4'-disodiosulfooxy-3'-aminoisoflavone

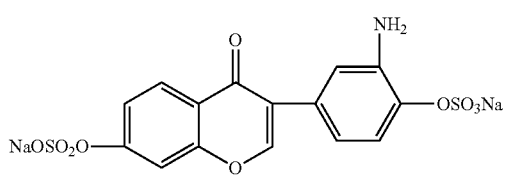

3.12 7-methoxy-3'-amino-4'-sodiosulfooxyisoflavone

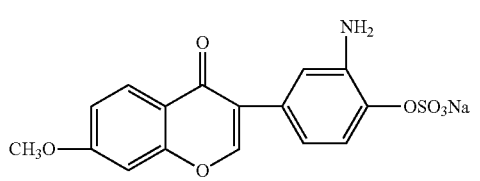

3.13 7-sodiosulfooxy-3'-amino-4'-methoxyisoflavone

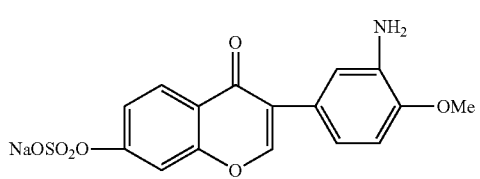

3.14 7-sodiosulfooxy-2'-amino-4'-methoxyisoflavone

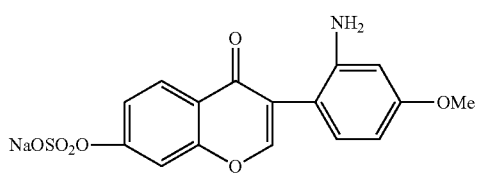

3.15 7,4'-disulfamoyloxy-3'-aminoisoflavone

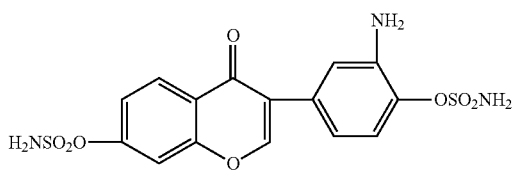

3.16 7,4'-disulfamoyloxy-2'-aminoisoflavone

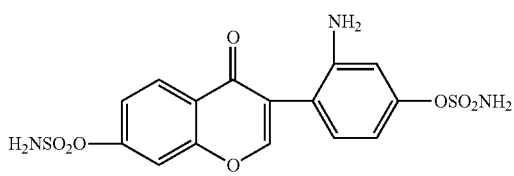

3.17 7-sulfamoyloxy-3'-amino-4'-methoxyisoflavone

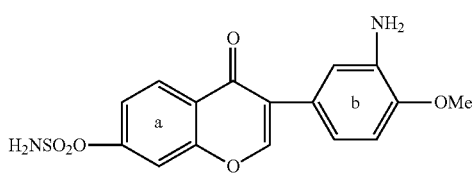

End Products

Example 3.18

7-sodiosulfooxy-3'-[(3,3-dimethyltriazenyl-1)-4'-methoxy)]isoflavone

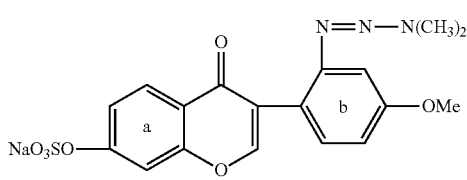

A solution composed of 2 g of sodium nitrite and 20 ml of water is added dropwise to a solution composed of 4 g (0.02 mol) of the aminoisoflavone from example 3.14, 30 ml of water and 5 ml of conc. hydrochloric acid at 0° C., the mixture is stirred for another 10 minutes and the resulting diazonium salt solution is quickly added dropwise to a solution composed of 8 g of sodium carbonate, 15 ml of water and 2 g of a 40% strength aqueous dimethylamine solution. The mixture is stirred for another 60 minutes, the crystalline reaction product is filtered off with suction and recrystallized from a little water.

The following triazenoisoflavones according to the invention are prepared in a manner analogous to example 3.18 from the abovementioned aminoisoflavones.

Example 3.19

7,4'-disodiosulfooxy-2'-(3,3-dimethyltriazenyl-1)isoflavone

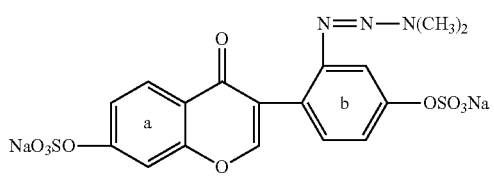

Example 3.20

7,4'-disodiosulfooxy-3'-(3,3-dimethyltriazenyl-1)isoflavone

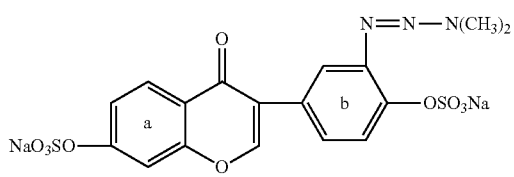

Example 3.21

7-methoxy-3'-(3,3-dimethyltriazenyl-1)-4'-sodiosulfooxyisoflavone

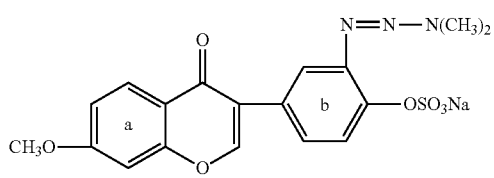

Example 3.22

7-sodiosulfooxy-3'-(3,3-dimethyltriazenyl-1)-4'-methoxyisoflavone

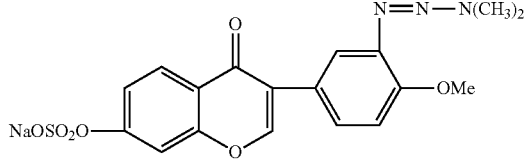

Example 3.23

7,4'-sulfamoyloxy-3'-(3,3-dimethyltriazenyl-1)isoflavone

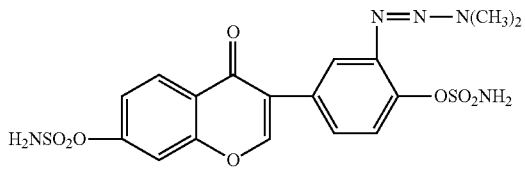

Example 3.24

7-sulfamoyloxy-2'-(3,3-dimethyltriazenyl-1)-4'-methoxyisoflavone

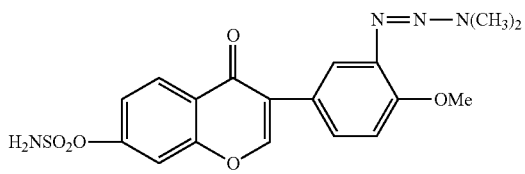

4. Diphenyl Derivatives (18) Which are Unbridged or Bridged by Atoms or Diatomic Groups:

Starting Materials:

Example 4.1

3-methyl-4-nitro-4'-(3-methyl-4-nitro-benzoyloxy)benzophenone

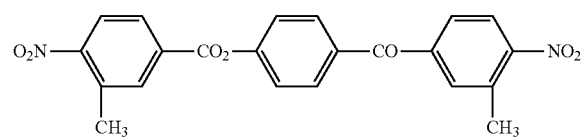

A mixture of 122 g of phenetole (1 mol), 400 g of 3-methyl-4-nitrobenzoyl chloride (2 mol) and 1500 ml of 1,2-dibromoethane is placed in a reaction vessel. 400 g of aluminum chloride are added in portions (exothermic!) at 15-20° C. while cooling. The reaction mixture is subsequently stirred stepwise at 20°-30° C., 40° C. and 80° C. for 2 hours in each case.

Work-up: cool reaction mixture to 0° C. and slowly introduce into 1.6 kg of ice. Then add 100 ml of conc. hydrochloric acid to the reaction mixture, stir and allow to stand. Decant off the supernatant solution and filter off the solid product with suction and wash with water.

Slurry the filter residue with 400 ml of acetone, cool to 0° C., filter off with suction and dry.

Purification: recrystallize from nitropropane

Example 4.2

4-hydroxy-3'-methyl-4'-nitrobenzophenone

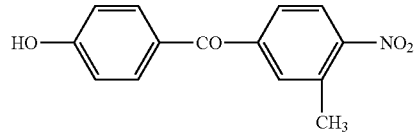

322 g (1 mol) of 4-nitro-4'-(4-nitrobenzoyloxy)benzophenone (example 4.1) are heated in 1.3 l of water, 200 ml of ethanol and 85 g of sodium hydroxide until the solid has dissolved.

Work-up: the reaction mixture is filtered hot through activated carbon/kieselguhr with suction. Onko 0640 is precipitated together with 4-nitrobenzoic acid from the filtrate by addition of 120 ml of concentrated hydrochloric acid. The solid is filtered off with suction and washed with water. The filter residue is stirred with 140 g of sodium hydrogencarbonate and 900 ml of water for 1 hour at 70, filtered off hot with suction, washed with 4 ml of hot water and dried.

Example 4.3

4-amino-3-methyl-4'-hydroxybenzophenone

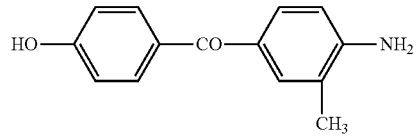 [SMILES: Cc1cc(C(=O)c2ccc(O)cc2)ccc1N]

25.8 g (0.1 mol) of 4-hydroxy-3'-methyl-4'-nitrobenzophenone (example 4.2) are dissolved in 200 ml of ethanol. At 80° C., a solution of 35 g of sodium sulfide in 40 ml of water is slowly added dropwise while stirring. The reaction solution is subsequently refluxed for 2 hours.

Work-up: the reaction solution is poured into 1 l of water, cooled to 20° C., and the precipitated product is filtered off with suction, dried and recrystallized from toluene.

Example 4.4

4-hydroxy-4'-(3,3-dimethyltriazenyl-1)benzophenone

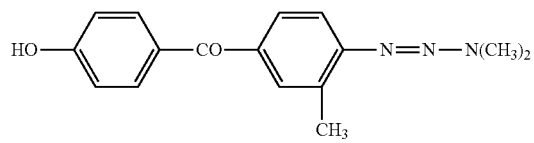 [SMILES: Cc1cc(C(=O)c2ccc(O)cc2)ccc1N=NN(C)C]

57 g (0.25 mol) of 4-amino-3-methyl-4'-hydroxybenzophenone are dissolved in a solution composed of 75 ml of concentrated hydrochloric acid and 400 ml of water. A solution composed of 25 ml of water and 17.25 g of sodium nitrite is then slowly added dropwise at from 0 to 5° C. while stirring. This diazonium salt solution is then added dropwise at from 0 to 5° C. while stirring to a solution produced from 75 g of sodium carbonate, 150 ml of water and 35 g of a 40% strength aqueous dimethylamine solution. The mixture is stirred for 1 hour, neutralized and the precipitated solid is filtered off with suction, dried and crystallized from n-hexane/toluene.

End Products

Example 4.5

4-(3,3-dimethyltriazenyl-1)-4'-sodiosulfooxy(diphenyl sulfone)

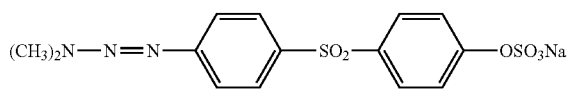

4 g (0.01 mol) of 4-hydroxy-4'-(3,3-dimethyltriazenyl-1)-(diphenyl sulfone) and 3.3 g (0.15 mol) of sodium bisulfate are admixed with 20 ml of dimethylformamide and 25 ml of tetrahydrofuran and stirred at room temperature for 30 hours. 20 ml of a 1 N aqueous sodium carbonate solution are then added to the reaction mixture, the mixture is stirred, the solid is filtered off with suction and the filtrate is evaporated under reduced pressure. The residue is dissolved in the minimum amount of water needed, filtered through activated carbon, the filtrate is evaporated on a rotary evaporator and the residue is recrystallized from methanol/water or a sodium chloride solution.

The following can be prepared in an analogous way:

Example 4.6

4-(3,3-dimethyltriazenyl-1)-2'-sodiosulfooxybenzophenone

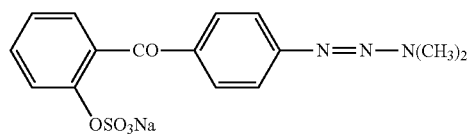

Example 4.7

2,6-dibromo-4-sodiosulfooxy-4'-(3,3-dimethyltriazenyl-1)-benzophenone

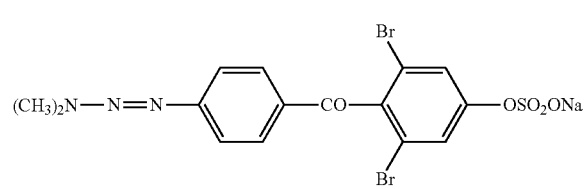

Example 4.8

2,6-dimethyl-4-sodiosulfooxy-4'-(3,3-dimethyltriazenyl-1)-benzophenone

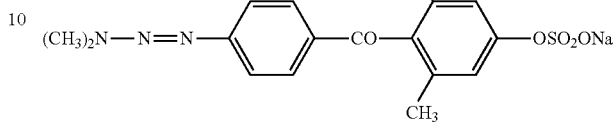

Example 4.9

4-(3,3-dimethyltriazenyl-1)-4'-sodiosulfooxybiphenyl

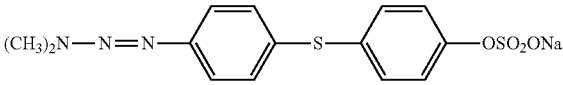

Example 4.10

4-(3,3-dimethyltriazenyl-1)-4'-sodiosulfooxy(diphenyl sulfide)

(CH₃)₂N—N=N—⟨⟩—S—⟨⟩—OSO₂ONa

Example 4.11

4-(3,3-dimethyltriazenyl-1)-4'-sodiosulfooxy(diphenyl sulfoxide)

(CH₃)₂N—N=N—⟨⟩—SO—⟨⟩—OSO₂ONa

Example 4.12

4-(3,3-dimethyltriazenyl-1)-4'-sodiosulfooxy(diphenyl sulfone)

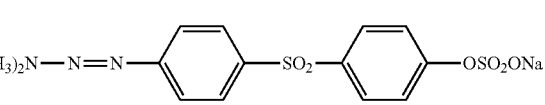

Example 4.13

4-(3,3-dimethyltriazenyl-1)-4'-sulfamoyloxybenzophenone

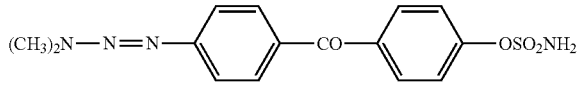

8.6 g (0.075 mol) of chlorosulfonamide are added dropwise to a solution of 13.4 g (0.05 mol) of 4-(3,3-dimethyltriazenyl-1)-4'-hydroxybenzophenone (example 4.6) in 100 ml of dimethylacetamide at 0° C. The mixture is stirred at 0° C. for 1 hour and subsequently at room temperature for another 12 hours. A saturated aqueous ammonium chloride solution is then added thereto, the mixture is extracted with ethyl acetate, dried over sodium sulfate, filtered and the solvent is taken off. The product is recrystallized from cyclohexane/ethyl acetate.

The following can be prepared in an analogous way:

Example 4.14

4-(3,3-dimethyltriazenyl-1)-2'-sulfamoyloxybenzophenone

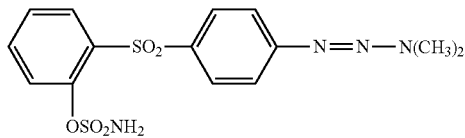

Example 4.15

4-(3,3-dimethyltriazenyl-1)-4'-sulfamoyloxy(diphenyl sulfoxide)

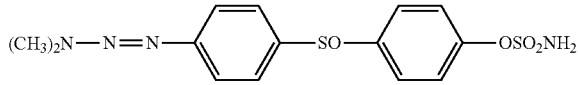

Example 4.16

4-(3,3-dimethyltriazenyl-1)-4'-sulfamoyloxy(diphenyl sulfone)

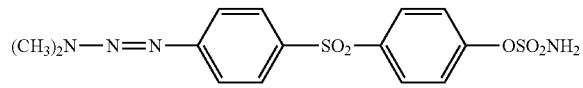

The invention claimed is:

1. A diphenyl derivative having the formula

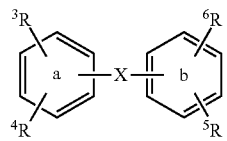

(18)

where
X is,
$R^3$, $R^6$ are each, independently of one another, hydrogen, hydroxyl, $C_1$-$C_4$-alkyl, $C_1$-$C_1$-alkoxy, $C_1$-$C_4$-alkyl-S—, $C_1$-$C_4$-alkyl-SO—, $C_1$-$C_4$-alkyl-$SO_2$—, halogen, nitro, cyano or an —$OSO_2Y$ group,
$R^4$, $R^5$ are each, independently of one another, an —N=N—N($R^2$)$_2$ group or an —$OSO_2Y$ group,
Y is OH, and
$R^2$ is methyl or ethyl,
with the proviso that, per total molecule (18), one or two —N=N—N($R^2$)$_2$ groups and one or two —$OSO_2Y$ groups are located on any ring carbons of aromatic rings, and also its salts, free acids, solvates and the solvates of these salts and the solvates of these free acids.

2. The diphenyl derivative as claimed in claim 1, the diphenyl derivative having the formula 4-(3,3-dimethyltriazenyl-1)-4'-sodiosulfooxybenzophenone

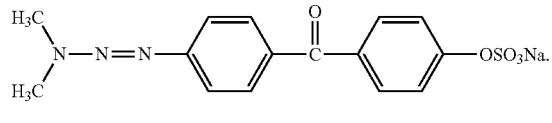

\* \* \* \* \*